US006541585B2

(12) United States Patent
Johnson et al.

(10) Patent No.: US 6,541,585 B2
(45) Date of Patent: Apr. 1, 2003

(54) POLYMERIZATION OF OLEFINS

(75) Inventors: Lynda Kaye Johnson, Wilmington, DE (US); Alison Margaret Anne Bennett, Wilmington, DE (US); Kerwin D. Dobbs, Wilmington, DE (US); Alex Sergey Ionkin, Kennett Square, PA (US); Steven Dale Ittel, Wilmington, DE (US); Ying Wang, West Chester, PA (US); Catherine E. Radzewich, Wilmington, DE (US); Lin Wang, Hockessin, DE (US); Elisabeth Hauptman, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/870,597

(22) Filed: May 31, 2001

(65) Prior Publication Data

US 2002/0037982 A1 Mar. 28, 2002

Related U.S. Application Data

(60) Provisional application No. 60/208,087, filed on May 31, 2000, provisional application No. 60/211,601, filed on Jun. 15, 2000, provisional application No. 60/214,036, filed on Jun. 23, 2000, and provisional application No. 60/264,537, filed on Jan. 26, 2001.

(51) Int. Cl.$^7$ .............................. C08F 4/44; C08F 4/16; C08F 10/02
(52) U.S. Cl. ................. 526/161; 526/171; 526/172; 526/178; 526/348; 526/352; 502/155; 502/167
(58) Field of Search .................. 526/161, 171, 526/172, 178, 348, 348.6, 352; 502/152, 155, 167

(56) References Cited

U.S. PATENT DOCUMENTS

| 6,103,658 A | 8/2000 | Mackenzie et al. |
| 6,133,387 A | * 10/2000 | Xu et al. .................... 526/172 |
| 6,174,975 B1 | 1/2001 | Johnson et al. |

FOREIGN PATENT DOCUMENTS

| WO | WO98/30609 | 7/1998 |
| WO | WO98/40374 A2 | 9/1998 |
| WO | WO98/47933 A1 | 10/1998 |
| WO | WO99/05189 A1 | 2/1999 |

OTHER PUBLICATIONS

Komon, Zachary J. A. et al., "Synthesis of butene–ethylene and hexene–butene–ethylene copolymers from ethylene via tandem action of well–defined homogeneous catalysts" J. Am. Chem. Soc. (2000), 122(8), 1830–1831.

M. M. Marques et al., Synthesis of polar vinyl monomer–olefin copolymers by α–diimine nickel catalyst, Polymer International (2001), 50, 579–587.

M. M. Marques et al., Macromol. Chem. Phys. (2000), 201, 2464–2468.

* cited by examiner

Primary Examiner—David W. Wu
Assistant Examiner—R. Harlan

(57) ABSTRACT

Polymers are produced using transition metal complexes that have sites capable of binding a Lewis acid in close proximity to the metal center.

23 Claims, No Drawings

POLYMERIZATION OF OLEFINS

CROSS-REFERENCE TO RELATED APPLICATION

This application claims priority under 35 U.S.C. §119 from U.S. Provisional Application Ser. No. 60/208,087 (filed May 31, 2000), No. 60/211,601 (filed Jun. 15, 2000), No. 60/214,036 (filed Jun. 23, 2000) and No. 60/264,537 (filed Jan. 26, 2001), all of which are incorporated by reference herein as if fully set forth.

FIELD OF INVENTION

Olefins including polar vinyl monomers, in particular acrylate monomers, are (co)polymerized using as catalysts selected transition metal complexes that have a Lewis acid in close proximity to the metal center.

TECHNICAL BACKGROUND

The polymerization of olefins such as ethylene and propylene is a very important commercial activity, and such polymers in various forms are made in enormous quantities for numerous uses. Various methods are known for polymerizing olefins, such as free radical polymerization of ethylene, and coordination polymerization using catalysts such as Ziegler-Natta-type and metallocene-type catalysts. Nevertheless, given the importance of polyolefins, new catalysts are constantly being sought for such polymerizations, to lower the cost of production and/or make new, and hopefully improved, polymer structures. More recently so-called single-site catalysts using late transition metal complexes have been developed, and they have proved in many instances to give polymers different in structure than those produced by the earlier known early transition metal catalysts.

Another type of useful polyolefin is one that contains polar comonomers, such as acrylates. One of the advantages of some late transition metal catalysts is that they can incorporate polar vinyl olefins, including acrylates, in copolymerizations with other polymerizable olefins, particularly ethylene.

It has been discovered that (co)polymers of olefins, including polar vinyl olefins, are produced especially well by transition metal complexes that contain ligands that are capable of binding a Lewis acid in close proximity to the transition metal center.

In general, Lewis acids are often added as activators to olefin polymerizations, e.g., for the purpose of transforming a halide or similar group on the metal into an alkyl group active for olefin insertion, for converting the metal complex into a cation species active for olefin polymerization, for protecting/deactivating the polar group of a monomer, and for scavenging impurities. In particular, the use of Lewis acids to activate late metal complexes for the copolymerization of ethylene and polar monomers and to protect the polar monomers has been reported; however, ligands that were capable of binding both a Lewis acid and a transition metal were not used in these copolymerizations. See, for example, U.S. Pat. No. 6,174,975; WO99/05189; M. M. Marques et. al., *Polym. Int.* (2001), 50, 579–587; and M. M. Marques, et. al. *Macromol. Chem. Phys.* (2000), 201, 2464–2468. Lewis acids have been added as activators for olefin polymerization to catalyst systems containing ligands that were capable of binding to the Lewis acid through a Lewis acid/Lewis base interaction (see for example, WO9840374, U.S. Pat No. 6,103,658 and WO9847933); however, no polar monomers were used in any of the copolymers made and, in addition, the ligand in these instances was not capable of binding the Lewis acid in close proximity to the metal center.

SUMMARY OF THE INVENTION

The invention concerns a process for polymerizing an olefin component comprising one or more polymerizable olefins, comprising the step of contacting, under polymerizing conditions, said olefin component with a polymerization catalyst system comprising a group 3–11 transition metal or lanthanide, a coordinating ligand, and a Lewis acid component, wherein the Lewis acid component is:

(a) neutral and covalently bound to said coordinating ligand, or (b) positively charged and bound to a Lewis basic site of said coordinating ligand.

Ethylene and $H_2C=CH-(CH_2)_t-H$ where t is an integer of 1 to 20 are more preferred olefins and ethylene is especially preferred.

In a preferred embodiment of the invention, the transition metal is Fe, Co, Ni, Pd or Cu; more preferably Ni. Preferably the polymerizable olefin is one or more of ethylene, $H_2C=CH-(CH_2)_t-H$, $H_2C=CH-R^{100}-G$, norbornene, substituted norbornene, cyclopentene, or substituted cyclopentene; where t is an integer of 1 to 20, and $R^{100}$ is a covalent bond or alkylene or substituted alkylene, and G is an inert functional group. Ethylene, $H_2C=CH-(CH_2)_t-H$, and $H_2C=CH-R^{100}-G$ are more preferred, and ethylene is especially preferred. It is preferred that $R^{100}$ is a covalent bond or $-(CH_2)_q-$, G is $C(O)Y$, Y is $-OH$, $-NR^{101}R^{102}$, $-OR^{103}$, or $-SR^{104}$, wherein $R_{101}$ and $R^{102}$ are each independently hydrogen, hydrocarbyl or substituted hydrocarbyl, $R^{103}$ and $R^{104}$ are each hydrocarbyl or substituted hydrocarbyl, and q is an integer of 1 to 20. Especially preferred are $R^{100}$ is a covalent bond, Y is $-OR^{103}$ and $R^{103}$ is an alkyl or substituted alkyl.

Preferably ethylene is homopolymerized or copolymerized with $H_2C=CH-(CH_2)_tH$ and/or $H_2C=CH-R^{100}G$. It is especially preferred that ethylene is copolymerized with $H_2C=CH-R^{100}G$.

In another embodiment, the ligand is capable of holding said Lewis acid in close proximity to said metal component. Preferably the Lewis acid is bound to the complex within a Lewis Acid Interaction Cone of about 130° or less; more preferably about 90° or less.

In another embodiment, the ligand is of the formula

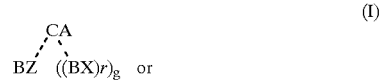

(I)

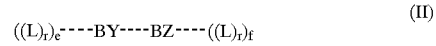

(II)

wherein BX, BY and BZ are each independently a Lewis base; L is independently LA or BX; LA is a Lewis acid; CA is a connecting atom selected from the group consisting of carbon, nitrogen, sulfur, silicon, boron, and phosphorus; f and r are independently an integer of 1 or more; e is zero or an integer of 1 or more; g is an integer of 2 or more; and dashed lines are bridges, single or multiple bonds.

In another embodiment, Formula (I) or (II) is

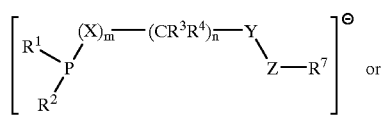

(III)

or

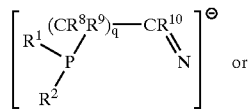

(IV)

or

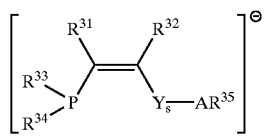

(V)

wherein:
R$^1$ and R$^2$ are each independently hydrocarbyl, substituted hydrocarbyl or a functional group;
Y is CR$^{11}$R$^{12}$, S(T), S(T)$_2$, P(T)Q, NR$^{36}$ or NR$^{36}$NR$^{36}$;
X is —O—, —CR$^5$R$^6$— or NR$^5$;
A is O, S, Se, N, P or As;
Z is O, S, Se, N, P or As;
each Q is independently hydrocarbyl or substituted hydrocarbyl;
R$^3$, R$^4$, R$^5$, R$^6$, R$^{11}$ and R$^{12}$ are each independently hydrogen, hydrocarbyl, substituted hydrocarbyl or a functional group;
R$^7$ is hydrogen, hydrocarbyl, substituted hydrocarbyl or a functional group, provided that when Z is O, S or Se, R$^7$ is not present;
each R$^8$ and R$^9$ is independently hydrogen, hydrocarbyl, substituted hydrocarbyl or a functional group;
R$^{10}$ is hydrogen, hydrocarbyl, substituted hydrocarbyl or a functional group;
R$^{11}$ and R$^{12}$ are each independently hydrogen, hydrocarbyl, substituted hydrocarbyl or a functional group;
each T is independently =O or =NR$^{30}$;
R$^{30}$ is hydrogen, hydrocarbyl, substituted hydrocarbyl, or a functional group;
each R$^{31}$ and R$^{32}$ is independently hydrogen, hydrocarbyl, substituted hydrocarbyl, or a functional group, provided that R$^{31}$ and R$^{32}$ taken together may form a ring;
R$^{33}$ and R$^{34}$ are each independently hydrocarbyl or substituted hydrocarbyl, provided that each is aryl substituted in at least one position vicinal to the free bond of the aryl group, or each has an E$_S$ of −1.0 or less;
R$^{35}$ is hydrogen, hydrocarbyl, substituted hydrocarbyl, or a functional group, provided that when A is O, S or Se, R$^{35}$ is not present;
R$^{36}$ is hydrogen, hydrocarbyl, substituted hydrocarbyl or a functional group;
m is 0 or 1;
s is 0 or 1;
n is 0 or 1; and
q is 0 or 1;
provided that:
any two of R$^3$, R$^4$, R$^5$, R$^6$, R$^8$, R$^9$, R$^{11}$ and R$^{12}$ bonded to the same carbon atom taken together may form a functional group;

any two of R$^1$, R$^2$, R$^3$, R$^4$, R$^5$, R$^6$, R$^7$, R$^8$, R$^9$, R$^{11}$, R$^{12}$, R$^{31}$, R$^{32}$, R$^{33}$, R$^{34}$, R$^{35}$ and R$^{36}$ bonded to the same atom or vicinal to one another taken together may form a ring.

In another preferred embodiment, Formula (III) is

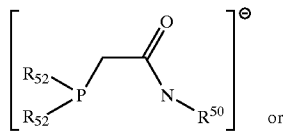

(VI)

or

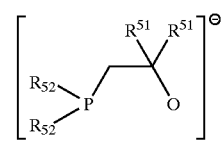

(VII)

wherein:
each R$^{52}$ is independently hydrocarbyl or substituted hydrocarbyl, provided that each R$^{52}$ is aryl substituted in one position vicinal to the free bond of the aryl group or each independently has an E$_S$ of −1.0 or less.
each R$^{50}$ is independently substituted hydrocarbyl; and
each R$^{51}$ is independently hydrogen, hydrocarbyl or substituted hydrocarbyl, provided that at least one of R$^{51}$ is substituted hydrocarbyl.

In another embodiment Formula (I) or (II) is

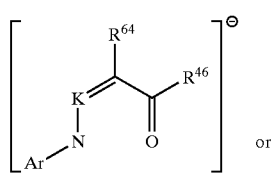

[VIII]

or

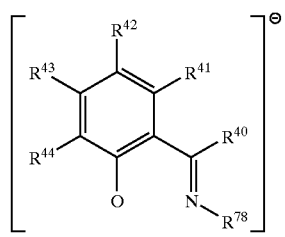

[IX]

wherein:
Ar is aryl or substituted aryl;
R$^{41}$, R$^{42}$, R$^{43}$ and R$^{44}$ are each independently hydrogen, hydrocarbyl, substituted hydrocarbyl or an inert functional group, and provided that any two of these groups vicinal to one another taken together may form a ring;
R$^{40}$ is hydrogen, hydrocarbyl or substituted hydrocarbyl;
K is N or CR$^{62}$;
R$^{46}$ is hydrocarbyl or substituted hydrocarbyl (such as —SR$^{67}$, —OR$^{67}$, or —N(R$^{68}$)$_2$, wherein R$^{67}$ is hydrocarbyl or substituted hydrocarbyl, and each R$^{68}$ is independently hydrogen, hydrocarbyl or substituted hydrocarbyl);
R$^{64}$ is hydrogen, a functional group, hydrocarbyl or substituted hydrocarbyl, and R$^{62}$ is hydrocarbyl or substituted hydrocarbyl, provided that R$^{62}$ and R$^{64}$, or R$^{64}$ and R$^{46}$, taken together may form a ring; and
R$^{78}$ is hydrocarbyl or substituted hydrocarbyl.

In another embodiment formula (I) or (II) is

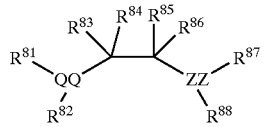
(X)

wherein:
ZZ is nitrogen or oxygen; and
QQ is nitrogen or phosphorous;
provided that:
when QQ is phosphorous and ZZ is nitrogen: $R^{81}$ and $R^{82}$ are each independently hydrocarbyl or substituted hydrocarbyl having an $E_S$ of about −0.90 or less; $R^{83}$, $R^{84}$, $R^{85}$, $R^{86}$ and $R^{87}$ are each independently hydrogen, hydrocarbyl or substituted hydrocarbyl; and $R^{88}$ is aryl or substituted aryl, provided than any two of $R^{81}$, $R^{82}$, $R^{83}$, $R^{84}$, $R^{85}$, $R^{86}$, $R^{87}$ and $R^{88}$ vicinal or geminal to one another together may form a ring;
when QQ is phosphorous and ZZ is oxygen: $R^{81}$ and $R^{82}$ are each independently hydrocarbyl or substituted hydrocarbyl having an $E_S$ of about −0.90 or less; $R^{83}$ and $R^{84}$ are each independently hydrogen, hydrocarbyl or substituted hydrocarbyl; $R^{85}$ and $R^{87}$ taken together form a double bond; $R^{88}$ is not present; and $R^{86}$ is hydrocarbyl or substituted hydrocarbyl (such as —$OR^{89}$ or —$NR^{90}R^{91}$, wherein $R^{89}$ is hydrocarbyl or substituted hydrocarbyl, and $R^{90}$ and $R^{91}$ are each independently hydrogen, hydrocarbyl or substituted hydrocarbyl);
when QQ is nitrogen: $R^{81}$ is hydrocarbyl or substituted hydrocarbyl having an $E_S$ of about −0.90 or less; $R^{82}$ and $R^{83}$ are each independently hydrogen, hydrocarbyl or substituted hydrocarbyl, or taken together form a ring or a double bond; $R^{84}$ is hydrogen, hydrocarbyl or substituted hydrocarbyl; ZZ is oxygen; $R^{86}$ and $R^{87}$ taken together form a double bond; $R^{88}$ is not present; $R^{86}$ is —$OR^{92}$, —$R^{93}$ or —$NR^{94}R^{95}$, wherein $R^{92}$ and $R^{93}$ are each independently hydrocarbyl or substituted hydrocarbyl, and $R^{94}$ and $R^{95}$ are each hydrogen, hydrocarbyl or substituted hydrocarbyl; provided that when $R^{82}$ and $R^{83}$ taken together form an aromatic ring, $R^{81}$ and $R^{84}$ are not present.

These and other features and advantages of the present invention will be more readily understood by those of ordinary skill in the art from a reading of the following detailed description. It is to be appreciated that certain features of the invention which are, for clarity, described below in the context of separate embodiments, may also be provided in combination in a single embodiment. Conversely, various features of the invention which are, for brevity, described in the context of a single embodiment, may also be provided separately or in any subcombination.

DETAILED DESCRIPTION OF THE PREFERRED EMBODIMENTS

The following definitions are used herein and should be referred to for claim interpretation.

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups (and alkyl groups) herein contain 1 to about 30 carbon atoms.

By "substituted hydrocarbyl" herein is meant a hydrocarbyl group that contains one or more substituent groups which are inert under the process conditions to which the compound containing these groups is subjected (e.g., an inert functional group, see below). The substituent groups also do not substantially detrimentally interfere with the polymerization process or operation of the polymerization catalyst system. If not otherwise stated, it is preferred that substituted hydrocarbyl groups herein contain 1 to about 30 carbon atoms. Included in the meaning of "substituted" are chains or rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group other than hydrocarbyl or substituted hydrocarbyl which is inert under the process conditions to which the compound containing the group is subjected. By inert is meant that the functional groups do not substantially deleteriously interfere with any process described herein that the compound in which they are present may take part in. Examples of functional groups include halo (fluoro, chloro, bromo and iodo), ether such as —$OR^{22}$, wherein $R^{22}$ is hydrocarbyl or substituted hydrocarbyl, silyl, substituted silyl, thioether, and tertiary amino. In cases in which the functional group may be near a transition metal atom, the functional group alone should not coordinate to the metal atom more strongly than the groups in those compounds that are shown as coordinating to the metal atom, that is, they should not displace the desired coordinating group.

By a "cocatalyst" or a "catalyst activator" is meant one or more compounds that react with a transition metal compound to form an activated catalyst species. One such catalyst activator is an "alkyl aluminum compound" which, herein, is meant a compound in which at least one alkyl group is bound to an aluminum atom. Other groups such as, for example, alkoxide, hydride and halogen may also be bound to aluminum atoms in the compound.

By "neutral Lewis base" is meant a compound, which is not an ion, that can act as a Lewis base. Examples of such compounds include ethers, amines, thioethers, and organic nitriles.

By "neutral Lewis acid" is meant a compound, which is not an ion, that can act as a Lewis acid. Examples of such compounds include boranes, alkylaluminum compounds, aluminum halides and antimony [V] halides.

By "cationic Lewis acid" is meant a cation that can act as a Lewis acid. Examples of such cations are sodium, lithium and silver cations.

By an "empty coordination site" is meant a potential coordination site on a transition metal atom that does not have a ligand bound to it. Thus if an olefin molecule (such as ethylene) is in the proximity of the empty coordination site, the olefin molecule may coordinate to the metal atom.

By a "ligand into which an olefin molecule may insert between the ligand and a metal atom", or a "ligand that may add to an olefin", is meant a ligand coordinated to a metal atom which forms a bond (L-M) into which an olefin molecule (or a coordinated olefin molecule) may insert to start or continue a polymerization. For instance, with ethylene this may take the form of the reaction (wherein L is a ligand):

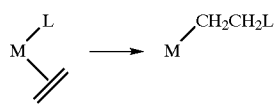

By a "ligand which may be displaced by an olefin" is meant a ligand coordinated to a transition metal which, when exposed to the olefin (such as ethylene), is displaced as the ligand by the olefin.

By a "monoanionic ligand" is meant a ligand with one negative charge.

By a "neutral ligand" is meant a ligand that is not charged.

By "aryl substituted in at least one position vicinal to the free bond of the aryl group," is meant the bond to one of the carbon atoms next to the free valence of the aryl group is something other than hydrogen. For example, for a phenyl group, it would mean the 2 position of the phenyl group would have something other than hydrogen attached to it. A 1-naphthyl group already has something other than hydrogen attached to one of the vicinal carbon atoms at the fused ring junction, while a 2-naphthyl group would have to be substituted in either the 1 or 3 positions to meet this limitation. A preferred aryl substituted in at least one position vicinal to the free bond of the aryl group is a phenyl group substituted in the 2 and 6 positions, and optionally in the other positions.

"Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By a "styrene" herein is meant a compound of the formula

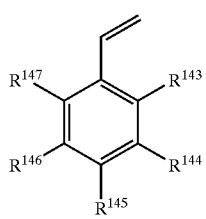

(XXXIV)

wherein $R^{143}$, $R^{144}$, $R^{145}$, $R^{146}$ and $R^{147}$ are each independently hydrogen, hydrocarbyl, substituted hydrocarbyl or a functional group, all of which are inert in the polymerization process. It is preferred that all of $R^{143}$, $R^{144}$, $R^{145}$, $R^{146}$ and $R^{147}$ are hydrogen. Styrene (itself) is a preferred styrene.

By a "norbornene" is meant a compound of the formula

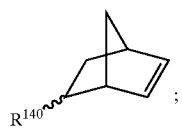

(XXXV)

wherein $R^{140}$ is hydrogen or hydrocarbyl containing 1 to 20 carbon atoms. It is preferred that $R^{140}$ is hydrogen or alkyl, more preferably hydrogen or n-alkyl, and especially preferably hydrogen. The norbornene may be substituted by one or more hydrocarbyl, substituted hydrocarbyl or functional groups in the $R^{140}$ or other positions, with the exception of the vinylic hydrogens, which remain. Norbornene (itself), dimethyl endo-norbornene-2,3-dicarboxylate and t-butyl 5-norbornene-2-carboxylate are preferred norbornenes, with norbornene (itself) being especially preferred.

By a "π-allyl group" is meant a monoanionic ligand comprised of 1 $sp^3$ and two $sp^2$ carbon atoms bound to a metal center in a delocalized $\eta^3$ fashion indicated by

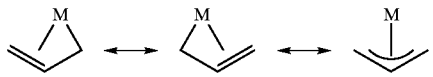

The three carbon atoms may be substituted with other hydrocarbyl groups or functional groups.

"Vinyl group" has its usual meaning.

By a "hydrocarbon olefin" is meant an olefin containing only carbon and hydrogen.

By a "polar (co)monomer" or "polar olefin" is meant an olefin which contains elements other than carbon and hydrogen. In a "vinyl polar comonomer," the polar group is attached directly to a vinylic carbon atom, as in acrylic monomers. When copolymerized into a polymer the polymer is termed a "polar copolymer". Useful polar comonomers are found in U.S. Pat. No. 5,866,663, WO9905189, WO9909078 and WO9837110, and S. D. Ittel, et al., Chem. Rev., vol. 100, p. 1169–1203(2000), all of which are incorporated by reference herein for all purposes as if fully set forth. Also included as a polar comonomer is CO (carbon monoxide).

By a "bidentate" ligand is meant a ligand which occupies two coordination sites of the same transition metal atom in a complex.

By a "tridentate" ligand is meant a ligand which occupies three coordination sites of the same transition metal atom in a complex.

By "$E_S$" is meant a parameter to quantify steric effects of various groupings, see R. W. Taft, Jr., J. Am. Chem. Soc., vol. 74, p. 3120–3128 (1952), and M. S. Newman, Steric Effects in Organic Chemistry, John Wiley & Sons, New York, 1956, p. 598–603, which are both hereby included by reference. For the purposes herein, the $E_S$ values are those described for o-substituted benzoates in these publications. If the value of $E_S$ for a particular group is not known, it can be determined by methods described in these references.

The transition metals preferred herein are in Groups 3 through 11 of the periodic table (IUPAC) and the lanthanides, especially those in the $4^{th}$ and $5^{th}$ periods, with Groups 8 through 11 being more preferred. Preferred transition metals include Ni, Pd, Fe, Co, Cu, Zr, Ti, and Cr with Ni, Pd, Fe, Co, and Cu being more preferred and Ni being especially preferred. Preferred oxidation states for some of the transition metals are Ti(IV), Ti(III), Zr(IV), Cr(III), Fe[II], Fe(III), Ni[II], Co[II], Co(III), Pd[II], and Cu[I] or Cu[II].

By "under polymerization conditions" is meant the conditions for a polymerization that are usually used for the particular polymerization catalyst system being used. These conditions include things such as pressure, temperature, catalyst and cocatalyst (if present) concentrations, the type of process such as batch, semibatch, continuous, gas phase, solution or liquid slurry etc., except as modified by conditions specified or suggested herein. Conditions normally done or used with the particular polymerization catalyst system, such as the use of hydrogen for polymer molecular weight control, are also considered "under polymerization conditions". Other polymerization conditions such as presence of hydrogen for molecular weight control, other polymerization catalysts, etc., are applicable with this polymerization process and may be found in the references cited herein.

The present invention is directed to the manufacture of a polymer by (co)polymerizing one or more polar vinyl olefins with optionally one or more polymerizable olefins, by contacting the olefins with a polymerization catalyst system under polymerization conditions; where the polymerization catalyst system comprises a transition metal component or a lanthanide, preferably a group 8–11 transition metal component, a coordinating ligand, and a Lewis acid component; wherein the Lewis acid component is (a) neutral and covalently bound to said coordinating ligand, or (b) positively charged and bound to a Lewis basic site of said coordinating ligand.

The term Lewis acid as used herein is as defined by G. N. Lewis ("An acid is an electron-pair acceptor"), and includes Bronsted acids, electrophilic metal centers, etc.

The term Lewis base as used herein is as defined by G. N. Lewis ("A base is an electron pair donor"), and includes a number of different donor atoms and groups including (but not limited to) phosphorus, nitrogen, oxygen, sulfur, halogens, Cp, Cp*, etc., with phosphorus, nitrogen and oxygen being especially preferred, as well as Brönsted bases. For definitions of Lewis acid and Lewis base, see *McGraw-Hill Encycl. of Technology*, $7^{th}$ Edition, Vol. 1, pg. 54–55.

While not wishing to be limited by theory, it is believed that one factor limiting the productivity of metal-catalyzed polar olefin copolymerizations is the Lewis acid/base interaction between the electrophilic metal center and the polar (often carbonyl oxygen) functionality after the polar olefin has been incorporated into a growing polymer chain. Therefore the Lewis acids present in the complexes of this invention should preferably be in a position (in 3 dimensions) to interact with this functionality, especially when a polar olefin, particularly a vinyl polar olefin, is present.

Dreiding Models (manufactured by Büchi Laboratory-Techniques, Ltd, Switzerland, and available in the USA from Aldrich Chemical Company. The Normal Set, Aldrich Catalog Number Z24,787-1 and the Porphyrin Set, Aldrich Catalog Number Z25,644-7, together provide the parts required for this purpose), or similar model systems of sufficient quality are a useful tool to understand the geometries of various catalytic complexes. They provide very precise bond distances and angles while maintaining all of the flexibility normally associated with atom-atom bonds. They are available with the metal, carbon, nitrogen, oxygen, phosphorus, sulfur and all other atoms necessary for building all of the ligands and complexes discussed herein. They also come with a convenient ruler to measure distance between atom centers in Angstroms. They are useful to determine the potential for interaction between the polar functionality on the growing polymer chain and any Lewis acidic site in the complex. Through rotation about the metal-C bond and any other C—C bonds in the polymer chain bound to the metal center, the polar functionality is able to sweep out a conical volume of space. If there is any available Lewis acidic site within that space (which may also rotate into that space), it is presumed that there can be a bonding interaction with that Lewis acidic site which would compete in an equilibrium with the metal center for the lone pair electrons on the polar functionality. The potential for interaction may be determined through the following construct of one embodiment of the catalyst systems used herein.

Starting with a square planar nickel atom, the complex is constructed by employing a ligand that can bind to two of the adjacent coordination sites on nickel through two donor groups or atoms, which are independently represented by L in the diagram below. A carbon atom is placed at a third site on nickel. The fourth coordination site on nickel is occupied by X, where X represents a ligand or a vacant coordination site.

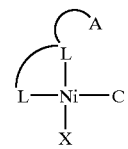

A solid cone is defined by the angle, θ, and the distance (in Å), λ, in the manner shown, with the axis of the cone along the nickel-carbon bond. The maximum value possible for θ is 180°.

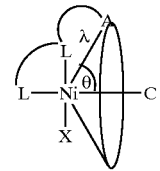

The conical volume of space through which the polar functionality attached to the growing polymer chain may sweep by means of rotation of the Ni—C and C—C bonds is determined through use of the models. This cone is the Lewis Acid Interaction Cone or LAIC. The angle increases for each additional carbon atom located between the nickel center and the polar functionality. For instance, in the case of methyl acrylate, θ varies from 65 to 120° in going from one to three carbon atoms between the nickel center and the carbonyl functionality.

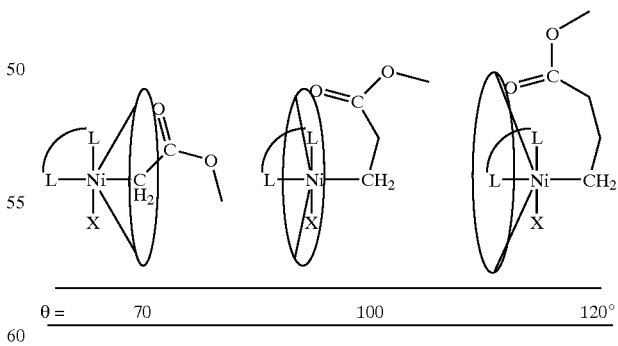

These are taken herein as typical values of the LAIC for a variety of commercially important polar olefins. Any catalyst complex having a Lewis acidic atom whose atomic center is within the LAIC is likely to bond to the electron pair available on the polar functionality. On the other hand, the Lewis acid in

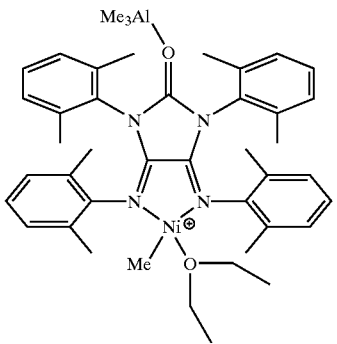

is well outside the LAIC even at θ=120° and will not be involved in binding to the Lewis-basic electron pair of the polar functionality, while the complex

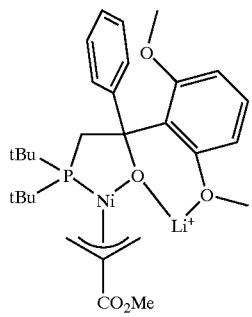

has the Lewis acidic Li$^+$ cation well within the LAIC even at θ=75°. To be an effective Lewis acid herein, the LAIC should be 130° or less, preferably about 120° or less, more preferably about 100° or less, and especially preferably about 90° or less. Clearly, other ligand steric effects may preclude the polar functionality from sweeeping out the entire three-dimensional volume of the cone, but the models will indicate whether a particular interaction is feasible.

The volume swept out by the rotating carbonyl is also limited in its distance, λ, from the nickel center. It may not come closer to nickel than the bonding distance of just over 2 Å. Maximizing the distance from the metal center, one observes 4.5, 5.0 and 6.5 Å, respectively for one, two and three carbons between nickel and the carbonyl group. These distances impose a further constraint upon the position of the Lewis acid, but the distance from the metal center is seldom a limitation in the construction of ligands.

Lewis acids useful for this purpose include metal salts of non-coordinating anions. Useful examples of metals for this application include but are not limited to Li, Na, K, Mg, Ca, Mn, Cu, and Zn. Preferred is Li. Also useful but seldom applied in commercial applications due to toxicity or cost are Ag, Tl, and Hg. Lanthanide metals, Ti, Zr, and V are also potentially useful. Noncoordinating anions include but are not limited to triflate, tetraphenylborate, hexafluoroantimonate, tetra(pentafluorophenyl)borate, tetrafluoroborate, $[CB_{11}H_6Cl_6]^-$, $[B(3,5-(CF_3)_2C_6H_3)_4]^-$ (BAF), $N[S(O)_2CF_3]_2^-$ and $[Al(OC_6F_5)_4]^-$. Preferred is BAF and tetra(pentafluorophenyl)borate. Some care must be taken in the choice of Lewis acids because some are also redox active in addition to being Lewis acids. For instance, $AgBF_4$ can act as a one electron oxidant.

The Lewis acid component may be neutral and covalently bound to the ligand coordinated to the nickel center. For example, a $Ph_2B^-$ group may be incorporated into the ligand structure. Alternatively, the coordinating ligand may incorporate some form of Lewis basic site or sites that will bind a positively charged Lewis acid. Thus, an appropriately situated carboxylate group and ether group might each contribute an oxygen atom donor to hold the cationic Lewis acid in place.

It is important in each of these examples that the ligand structure not satisfy all of the coordination sites on the Lewis acid when a polar olefin, particularly a vinyl polar olefin, is present. There must be one coordination site left available for coordination of the polar functionality of the incoming polar monomer or the polar functionality of the polar group after it has been incorporated into the growing polymer chain. Thus, boron or lithium atoms must be tri-coordinate, not tetracoordinate. Sodium atoms must be no more than tetracoordinate. The nuclearity of the Lewis acids may also vary in that two or more Lewis acid centers might be bridged by Lewis base donors, though one coordination site must remain available.

The most accurate method of determining the mode of bonding in complexes bearing Lewis acids is by means of X-ray or neutron crystallography. Specific bond distances and angles may be determined quite reliably. The method does, however, require that suitable crystals can be grown. The method also assumes that the solid state structure reflects the catalyst structure in solution, though this is generally a safe assumption. EXAFS can be employed to determine interatomic distances and the elements in the first coordination sphere of a catalyst complex. EXAFS is most useful for the determination of positions of heavier element Lewis acids. In addition to scattering or diffraction techniques, NMR spectroscopy provides several approaches to the determination of catalyst structure. Many of the nucleii involved in this chemistry are magnetically active, providing multiple approaches to the problem. It is sometimes possible to directly observe magnetic coupling between adjacent nucleii, confirming points of coordination or attachment. Specific interionic contacts and estimates of average interionic distances may be determined for solution species by NOE NMR measurements (see C. Zuccaccia, G. Bellachioma, G. Cardaci, and A. Macchioni, *Organometallics* (1999), 18(1), 1). In addition, it is often possible to detect the presence of Lewis acid adducts of carbonyl groups through diagnostic shifts in the infrared spectra carried out in the presence and absence of the Lewis acid or in the presence of a variety of Lewis acids. Computational chemistry can often provide useful insight into the location and coordination geometry of organometallic complexes and their Lewis acid adducts. Finally, it is always possible to quantify the rate and yield of polymerization and the degree of comonomer incorporation in the presence and absence of a given Lewis acid or in the presence of a selection of Lewis acids and the comparison will be indicative of the role of the Lewis acid.

More preferred forms of the ligands used in the present invention are ligands of the Formulas I or II:

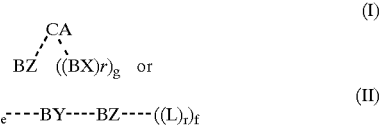

wherein BX, BY and BZ are each independently a Lewis base; each L is independently LA or BX; LA is a Lewis acid; CA is a connecting atom selected from the group consisting of carbon, nitrogen, sulfur, silicon, boron, and phosphorus;

f and r are independently an integer of 1 or more; e is zero or an integer of 1 or more; g is an integer of 2 or more; and dashed lines, herein referred to as arms, are bridges, single or multiple bonds. A bridge is herein defined as one or more atoms that connect two or more other atoms, connected by single or multiple bonds.

When two Lewis bases of a ligand of Formula I or II bind to the same transition metal center and occupy two adjacent coordination sites of that metal center, the ligand and the metal center will form a ring. Additionally, when two Lewis bases of a ligand of Formula I or II bind to the same Lewis acid, the ligand and the Lewis acid will form a ring. For these said rings, ring sizes of 3–7 are preferred, with 5- and 6-membered rings being especially preferred.

More specifically, ligands of Formula I are comprised of ligands containing two or more arms radiating from a central connecting atom CA, and the number of these said bonds or arms is represented by g with g being an integer of 2 or more. Each of these said arms is covalently bonded to one or more Lewis bases $BX_h$, wherein each $BX_h$ is independently chosen from BX. The number of Lewis bases within each arm is represented by $r_i$, wherein the value of each $r_i$ is independently an integer of 1 or more and i is an integer of 1 to g; h is then an integer of 1 to the sum of $(r_1+r_2+ \ldots +r_g)$. In addition, another arm radiates from CA and is covalently bonded to a Lewis base BZ. The illustrations below exemplify ligands of Formula I with different values of g and $r_i$ and different numbers of Lewis bases $BX_h$ incorporated.

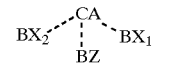
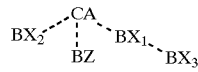

In the above illustrations and in those to follow of ligands of Formulas (I) and (II), it is not our intent to limit the connectivity of the bases BX or Lewis acids LA within the same arm of a ligand to that which is specifically illustrated. For example, the two structures directly below fulfill the requirements of ligands of Formula I with g=2 and $r_1$=2 and $r_2$=1.

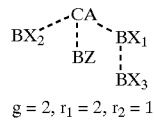
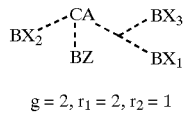

More specifically, ligands of Formula (II) are comprised of ligands containing two Lewis bases BY and BZ that are covalently bonded to each other through an arm. One or more additional arms radiate from BZ and the number of these said arms is represented by f, with f being an integer of 1 or more. Optionally, one or more additional arms radiates from BY and the number of these said arms is represented by e with e being zero or an integer of 1 or more. Each of these said arms is covalently bonded to one or more $L_h$, wherein each $L_h$ is independently a Lewis base BX or a Lewis acid LA. The number of independent $L_h$ within each arm is represented by $r_i$, wherein the value of each $r_i$ is independently an integer of 1 or more, and i is an integer of 1 to the sum of (e+f); h is then an integer of 1 to the sum of $(r_1+r_2+ \ldots r_{(e+f)})$. The illustrations below exemplify ligands of Formula II with different values of e, f and $r_i$ and $L_h$.

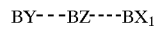

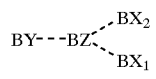
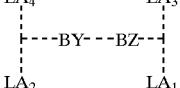

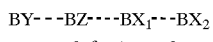
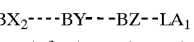

Illustrative, but not limiting, general representations of possible binding modes of ligands of Formula (I) and Formula (II) to both a transition metal and a Lewis acid are shown below. These representations illustrate some of the possible products and binding modes that may have formed during the synthesis of the ligand and the subsequent synthesis of the metal compound and the Lewis acid complex and are not meant to be restrictive. In these structures straight lines are either single or multiple bonds and dashed lines are bridges, single or multiple bonds.

The structures below show general representations of possible binding modes of ligands of Formula I where the ligand is bound in a bidentate fashion and a tridentate fashion to the metal center. Examples of CA--BZ include, but are not limited to, C=O, C=$N^-$, C=$P^-$, N—O, S=O, S=$N^-$, C—$O^-$, Si—$O^-$, C—$S^-$, Si—$S^-$, $B^\frown O^-$, $B^\frown N^{2-}$, P=O, $C^\frown O^-$, $C^\frown N^{2-}$, where ^ represents a bridge.

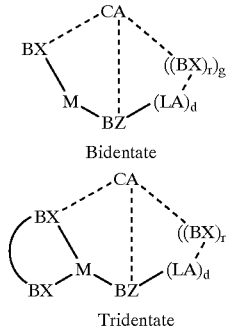

Bidentate

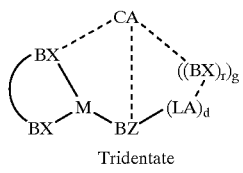

Tridentate

More specific illustrative, but not limiting, representations of the bidentate structures are shown below. Similar illustrative representations could be drawn in an analogous fashion for the tridentate structures. In these illustrations, R=hydrogen, hydrocarbyl, substituted hydrocarbyl or a functional group.

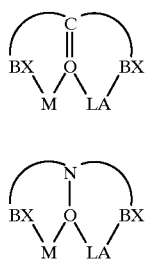
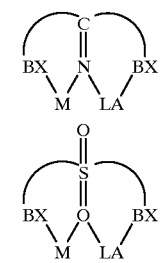
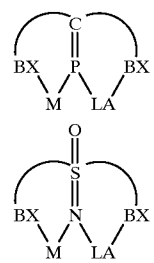

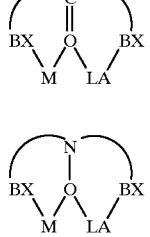
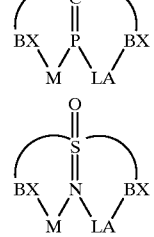

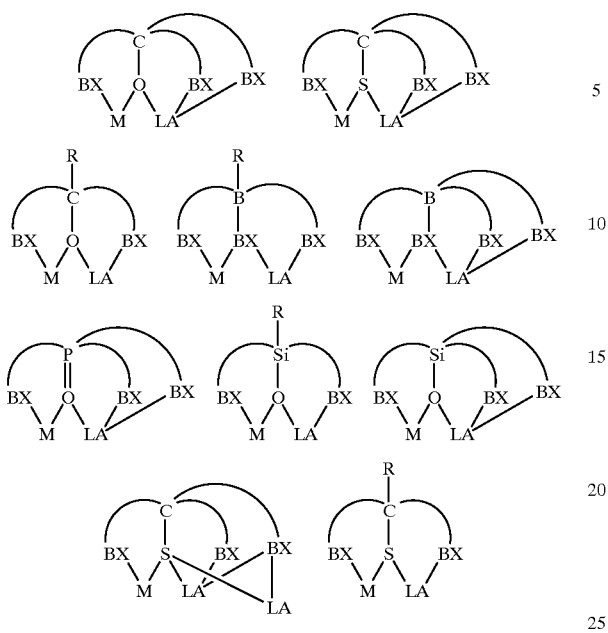

The structures below show general examples of possible binding modes of ligands of Formula (II) where the ligand is bound in a bidentate fashion and a tridentate fashion to the metal center. In these structures, LA' means $(LA)_d$ or $(BX)_{r-}(LA)_d$, wherein d is an integer of one or more.

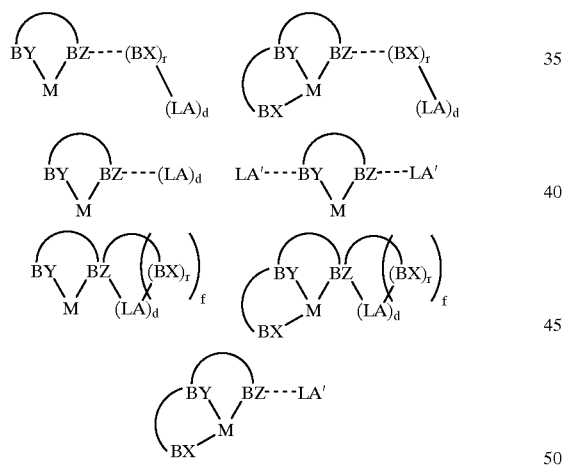

More specific illustrative, but not limiting, representations of some of the above structures are shown below. Similar illustrative representations could be drawn in an analogous fashion for the other structures.

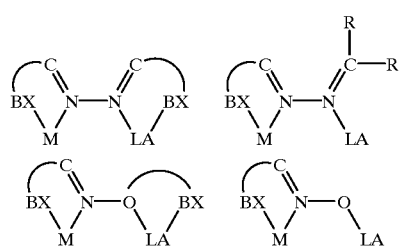

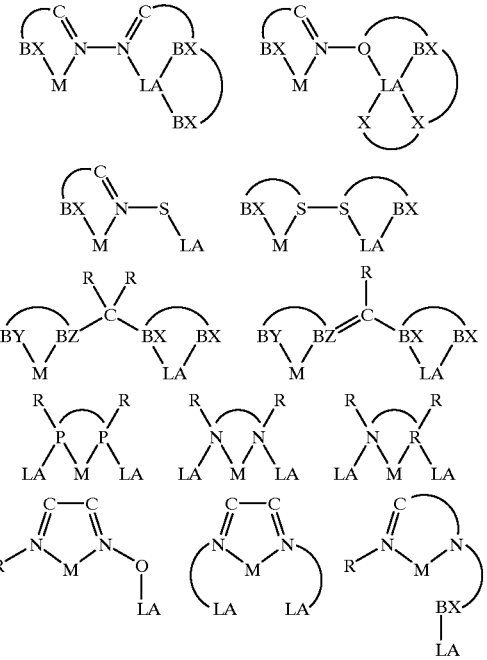

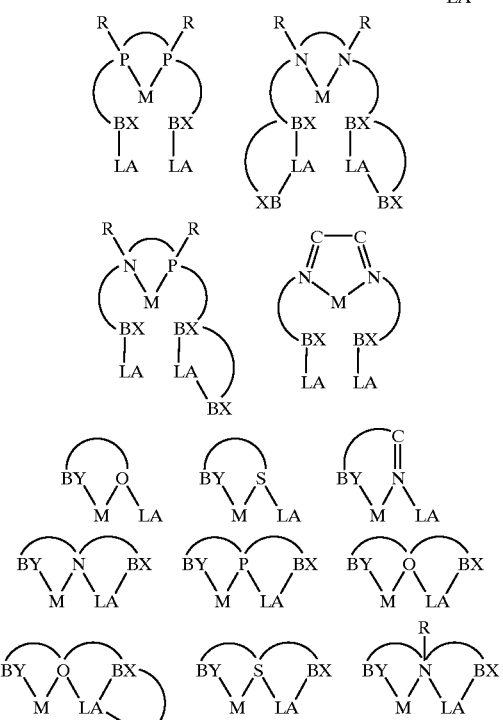

In general, numerous methods can be utilized in order to synthesize specific ligands of Formula I and II, as exemplified further below. For example, a Lewis-base-containing nucleophile can be added to a Lewis-base-containing electrophile, e.g., such as in the addition of (t-Bu)2PCH2Li to 2,4-dimethoxyphenylisocyanate and to 2,4,6-trimethoxbenzophenone, as illustrated in the Examples. Alternatively, two equivalents of a Lewis-base-containing nucleophile can be added to an electrophile with a leaving group such a RC(O)X where X=halide, hydrocarbyloxy, etc. to give a ligand of Formula I with two identical donor arms. This is illustrated in the Examples by the addition of two equivalents of (t-Bu)$_2$PCH$_2$Li to RC(O)X to give [t-Bu)$_2$ PCH$_2$)$_2$RC—O]$^-$. Condensation of an aniline with a ketone or aldehyde containing an additonal Lewis base, such as the addition of respectively one and two equivalents of aniline to 2-methoxyethyl acetoacetate and 2-hydroxy-5-methyl-1, 3-benzenedicarboxaldehyde, as illustrated in the examples, enables the synthesis of ligands of Formula (I) based upon imines. Alternatively, the aniline itself might contain an additional Lewis base. The condensation of such an aniline with a diketone would lead to ligands of Formula (II). In another synthetic method, a bis(nucleophile) containing a central Lewis base can be added to two equivalents of a Lewis-base containing electrophile to give ligands of Formula (I). Such a strategy is illustrated in the Examples by the addition the dianion of 2-indanone to two equiv of (t-Bu)$_2$ PCl.

Transition metal complexes having neutral ligands can be made by a variety of methods. See, for instance, U.S. Pat. No. 5,880,241, which is incorporated by reference herein for all purposes as if fully set forth. In part, how such compounds are made depends upon the transition metal compound used in the synthesis of the complex and upon what each anion in the final product is. For example, for transition metals such as Ni[II], Fe[II], Co[II], Ti[IV] and Zr[IV], a metal halide precursor such as the chloride may be mixed with the neutral ligand, resulting in a transition metal complex wherein the anion is halide. When it is desired that one of the anions be a relatively noncoordinating anion and another is an anion which may add across an olefinic bond (as in ethylene), for example using a nickel compound, then nickel allyl halide dimer may be mixed with a neutral ligand in the presence of an alkali metal salt of a relatively noncoordinating anion such as sodium tetrakis[3,5-bistrifluoromethylphenyl]borate (BAF for the anion alone) to form a complex in which one anion is π-allyl and the other anion BAF. Transition complexes having anionic ligands can be made by a variety of similar methods, except that the ligand now fulfills one of the negative valences of the metal complex. Other useful nickel precursors and methods of synthesis of nickel complexes with both neutral and anionic ligands may be found in previously incorporated S. D. Ittel, et al., *Chem. Rev.*, vol. 100, pp. 1169–1203 (2000), and references therein.

A preferred embodiment is where Formula (I) or (II) is

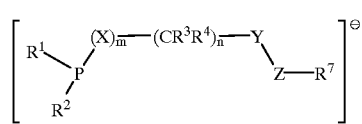

(III)

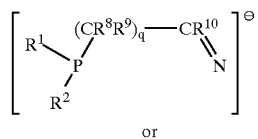

(IV)

or

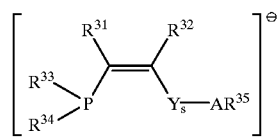

(V)

-continued wherein:

R$^1$ and R$^2$ are each independently hydrocarbyl, substituted hydrocarbyl or a functional group;

Y is CR$^{11}$R$^{12}$, S(T), S(T)$_2$, P(T)Q, NR$^{36}$ or NR$^{36}$—NR$^{36}$;

X is —O—, —CR$^5$R$^6$— or NR$^5$;

A is O, S, Se, N, P or As;

Z is O, S, Se, N, P or As;

each Q is independently hydrocarbyl or substituted hydrocarbyl; R$^3$, R$^4$, R$^5$, R$^6$, R$^{11}$ and R$^{12}$ are each independently hydrogen, hydrocarbyl, substituted hydrocarbyl or a functional group;

R$^7$ is hydrogen, hydrocarbyl, substituted hydrocarbyl, or a functional group, provided that when Z is O, S or Se, R$^7$ is not present;

each R$^8$ and R$^9$ is independently hydrogen, hydrocarbyl, substituted hydrocarbyl or a functional group;

R$^{10}$ is hydrogen, hydrocarbyl, substituted hydrocarbyl, or a functional group;

R$^{11}$ and R$^{12}$ are each independently hydrogen, hydrocarbyl, substituted hydrocarbyl or a functional group;

each T is independently =O or =NR$^{30}$;

R$^{30}$ is hydrogen, hydrocarbyl, substituted hydrocarbyl, or a functional group;

each R$^{31}$ and R$^{32}$ is independently hydrogen, hydrocarbyl, substituted hydrocarbyl, or a functional group, provided that R$^{31}$ and R$^{32}$ taken together may form a ring;

R$^{33}$ and R$^{34}$ are each independently hydrocarbyl or substituted hydrocarbyl, provided that each is aryl substituted in at least one position vicinal to the free bond of the aryl group, or each has an E$_S$ of −1.0 or less;

R$^{35}$ is hydrogen, hydrocarbyl, substituted hydrocarbyl, or a functional group, and provided that when A is O, S or Se, R$^{35}$ is not present;

R$^{36}$ is hydrogen, hydrocarbyl, substituted hydrocarbyl, or a functional group;

m is 0 or 1;

s is 0 or 1;

n is 0 or 1; and q is 0 or 1;

and provided that:

any two of R$^3$, R$^4$, R$^5$, R$^6$, R$^8$, R$^9$, R$^{11}$ and R$^{12}$ bonded to the same carbon atom taken together may form a functional group;

any two of R$^1$, R$^2$, R$^3$, R$^4$, R$^5$, R$^6$, R$^7$, R$^8$, R$^9$, R$^{11}$, R$^{12}$, R$^{31}$, R$^{32}$, R$^{33}$, R$^{34}$, R$^{35}$ and R$^{36}$ bonded to the same atom or vicinal to one another taken together may form a ring.

Another preferred embodiment is where Formula (III) is

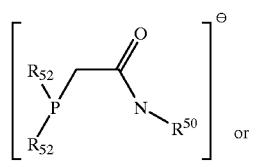
(VI)

or

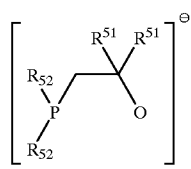
(VII)

wherein:
each $R^{52}$ is independently hydrocarbyl or substituted hydrocarbyl, provided that each $R^{52}$ is aryl substituted in one position vicinal to the free bond of the aryl group or each independently has an $E_S$ of −1.0 or less;
each $R^{50}$ is independently substituted hydrocarbyl; and
each $R^{51}$ is independently hydrogen, hydrocarbyl or substituted hydrocarbyl provided that at least one of $R^{51}$ is substituted hydrocarbyl.

A preferred process using ligands of Formula (VI) and (VII) is when the transition metal is Ni; the polymerizable olefins are selected from one or more of ethylene, $H_2C=CH-(CH_2)_tH$, and $H_2C=CHR^{100}G$, wherein t is an integer of 1 to 20 and $R^{100}$ is a covalent bond or alkylene or substituted alkylene and G is an inert functional group, and said coordinating ligand is capable of holding said Lewis acid in close proximity to said metal component. Especially preferred is the process when the polar vinyl olefin of the formula $H_2C=CHC(O)OR^{103}$ is copolymerized with ethylene, wherein $R^{103}$ is alkyl or substituted alkyl. The Lewis acid is more preferably a cation.

The ligands (III) and (IV) may be synthesized by a variety of methods, depending on the particular ligand desired. The synthesis of many specific ligands is illustrated in the Examples. Many of these syntheses are accomplished through the use of $R_2PLi$ or $R_2PCH_2Li$. More generally speaking, the synthesis of various types of ligands is illustrated in the schemes shown below. In these schemes, each R and/or R' independently represents hydrogen, hydrocarbyl or substituted hydrocarbyl.

Scheme 1

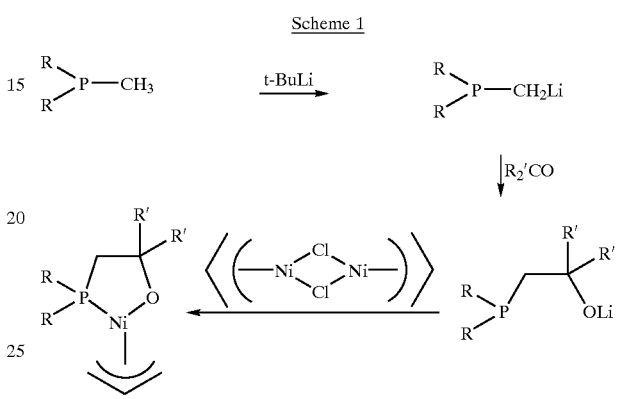

In Scheme 1 one may substitute an imine for the ketone $R'_2CO$ and obtain a final product in which Z is nitrogen rather than oxygen. In another variation of Scheme 1, one can react $R_2PH$ with an acrylonitrile, followed by reaction with R'MgX (addition across the nitrile bond) and then [(allyl)NiCl]$_2$ to form the 6-membered metallocycle in which Z is nitrogen. To obtain compounds in which Z is not nitrogen or oxygen, one can use analogous compounds containing the appropriate element for Z.

Scheme 2

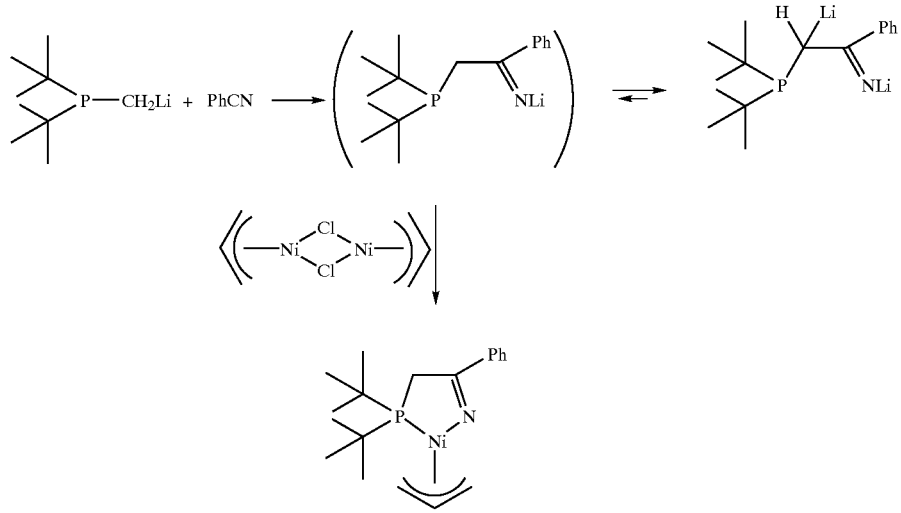

Scheme 2 shows the synthesis of (IV). Appropriate substitution (as in all these synthesis schemes) in these compounds may be obtained by using appropriately substituted starting materials.

Scheme 3

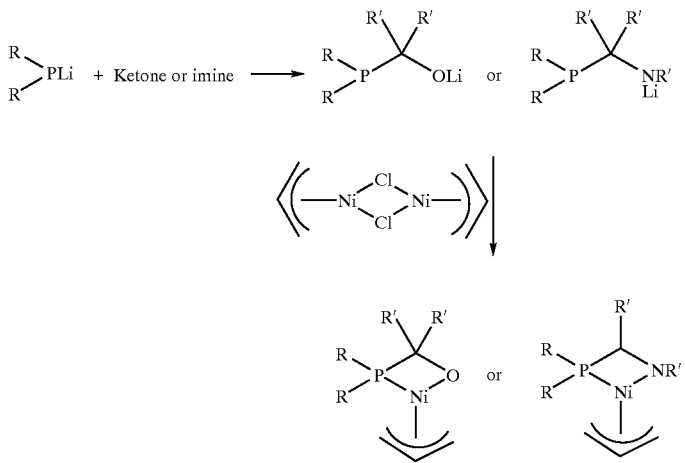

Scheme 3 shows the synthesis of 4-membered (or isomeric) metallocycles. Herein by isomeric is meant (and included in the definition of) that 4-membered heterocycles may also be in the form of bridged dimers and/or oligomers. Z may be changed by using the appropriate starting material.

Scheme 4

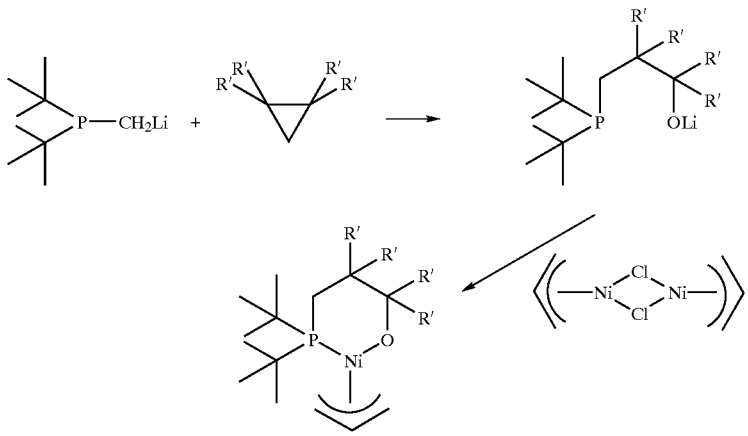

Scheme 4 illustrates the synthesis of a 6-membered metallocycle. The corresponding nitrogen compound may be made by using an aziridine as a starting material.

Scheme 5

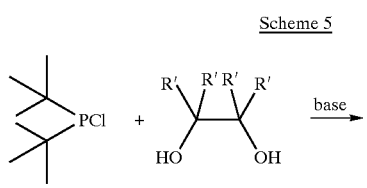

-continued

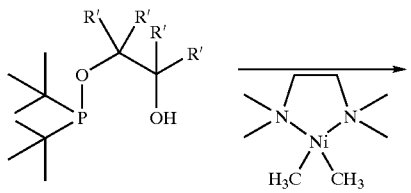

-continued

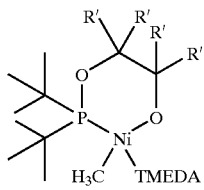

Scheme 5 illustrates a method for making III in which X is —O—. Herein TMEDA is tetramethylethylenediamine.

In Schemes 1–5 above Ni complexes are prepared, and for making late transition metal complexes other than Ni, similar reactions of metal compounds with an appropriate anion may be used to prepare the complex. Useful types of Ni compounds are listed below:

$(Ph_3P)_2Ni(Ph)(Cl)$, which gives as ligands Ph and $Ph_3P$;

$(TMEDA)_2Ni(Ph)(Cl)$ in the presence of a "trapping ligand" $L^2$ such as pyridine, which gives as ligands Ph and pyridine;

$(Ph_3P)_2NiCl_2$, which gives as ligands Cl and $Ph_3P$; and $[(allyl)Ni(X)]_2$, which gives as a ligand π-allyl.

Methods of synthesis of these types of nickel complexes may also be found in previously incorporated U.S. Pat. Nos. 6,060,569 and 6,174,975, as well as WO9842664 and R. H. Grubbs., et al., *Organometallics*, vol. 17, p. 3149 (1988), and references therein, which are also incorporated herein by reference for all purposes as if fully set forth.

Further general details on Formulas (III), (IV), (V), (VI) and (VII) can be found in U.S. patent application Ser. No. 09/871,099 (filed concurrently on May 31, 2001, which is incorporated by reference herein for all purposes as if fully set forth.

In another embodiment, Formula (I) or (II) is

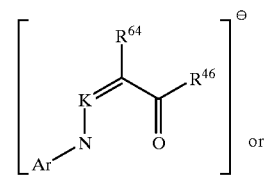

[VIII]

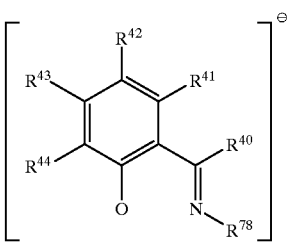

[IX]

wherein:
Ar is aryl or substituted aryl;
$R^{41}$, $R^{42}$, $R^{43}$ and $R^{44}$ are each independently hydrogen, hydrocarbyl, substituted hydrocarbyl or an inert functional group, provided that any two of these groups vicinal to one another taken together may form a ring;
$R^{40}$ is hydrogen, hydrocarbyl or substituted hydrocarbyl;
K is N or $CR^{62}$;
$R^{46}$ is hydrocarbyl or substituted hydrocarbyl (such as —$SR^{67}$, —$OR^{67}$ or —$NR^{68}_2$, wherein $R^{67}$ is hydrocarbyl or substituted hydrocarbyl, and each $R^{68}$ is independently hydrogen, hydrocarbyl or substituted hydrocarbyl);

$R^{64}$ is hydrogen, a functional group, hydrocarbyl or substituted hydrocarbyl, and $R^{62}$ is hydrocarbyl or substituted hydrocarbyl, and provided that $R^{62}$ and $R^{64}$, or $R^{64}$ and $R^{46}$, taken together may form a ring; and $R^{78}$ is hydrocarbyl or substituted hydrocarbyl.

In a preferred embodiment using ligands of Formula (VIII) or (IX), $R^{46}$ and $R^{44}$ are substituted hydrocarbyl, the transition metal is Ni; the polymerizable olefins are selected from one or more of ethylene, $H_2C=CH-(CH_2)_tH$, and $H_2C=CHR^{100}G$, wherein t is an integer of 1 to 20 and $R^{100}$ is a covalent bond or alkylene or substituted alkylene and G is an inert functional group and said coordinating ligand is capable of holding said Lewis acid in close proximity to said metal component. Especially preferred is the process when the polar vinyl olefin of the formula $H_2C=CHC(O)OR^{103}$ is copolymerized with ethylene, wherein $R^{103}$ is alkyl or substituted alkyl. The Lewis acid is more preferably a cation.

Further details on (VIII) and (IX), transition metal complexes thereof, and methods of making, may be found in previously incorporated U.S. Pat. No. 6,174,975.

In another embodiment the ligand is of the formula (X)

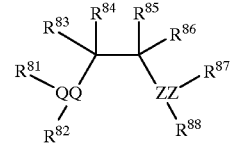

(X)

wherein:
ZZ is nitrogen or oxygen; and
QQ is nitrogen or phosphorous;
provided that:
when QQ is phosphorous and ZZ is nitrogen: $R^{81}$ and $R^{82}$ are each independently hydrocarbyl or substituted hydrocarbyl having an $E_S$ of about –0.90 or less; $R^{83}$, $R^{84}$, $R^{85}$, $R^{86}$ and $R^{87}$ are each independently hydrogen, hydrocarbyl or substituted hydrocarbyl; and $R^{88}$ is aryl or substituted aryl, provided that any two of $R^{81}$, $R^{82}$, $R^{83}$, $R^{84}$, $R^{85}$, $R^{86}$, $R^{87}$ and $R^{88}$ vicinal or geminal to one another together may form a ring;

when QQ is phosphorous and ZZ is oxygen: $R^{81}$ and $R^{82}$ are each independently hydrocarbyl or substituted hydrocarbyl having an $E_S$ of about –0.90 or less; $R^{83}$ and $R^{84}$ are each independently hydrogen, hydrocarbyl or substituted hydrocarbyl; $R^{85}$ and $R^{87}$ taken together form a double bond;

$R^{88}$ is not present; and $R^{86}$ is hydrocarbyl or substituted hydrocarbyl (such as —$OR^{89}$ or —$NR^{90}R^{91}$, wherein $R^{89}$ is hydrocarbyl or substituted hydrocarbyl, and $R^{90}$ and $R^{91}$ are each independently hydrogen, hydrocarbyl or substituted hydrocarbyl);

when QQ is nitrogen: $R^{81}$ is hydrocarbyl or substituted hydrocarbyl having an $E_S$ of about –0.90 or less; $R^{82}$ and $R^{83}$ are each independently hydrogen, hydrocarbyl or substituted hydrocarbyl, or when taken together may form a ring or a double bond; $R^{84}$ is hydrogen, hydrocarbyl or substituted hydrocarbyl; ZZ is oxygen; $R^{86}$ and $R^{87}$ taken together form a double bond; $R^{88}$ is not present; $R^{85}$ is —$OR^{92}$, —$R^{93}$ or —$NR^{94}R^{95}$, wherein $R^{92}$ and $R^{93}$ are each independently hydrocarbyl or substituted hydrocarbyl, and $R^{94}$ and $R^{95}$ are each hydrogen, hydrocarbyl or substituted hydrocarbyl; provided that when $R^{82}$ and $R^{83}$ taken together form an aromatic ring, $R^{81}$ and $R^{84}$ are not present.

A preferred form is where QQ is phosphorous and ZZ is oxygen.

In a preferred embodiment using ligands of Formula (X), one or more of $R^{81}$ through $R^{88}$ is substituted hydrocarbyl, the transition metal is Ni; the polymerizable olefins are selected from one or more of ethylene, $H_2C=CH-(CH_2)_t$H, and $H_2C=CHR^{100}G$, wherein t is an integer of 1 to 20 and $R^{100}$ is a covalent bond or alkylene or substituted alkylene and G is an inert functional group, and said coordinating ligand is capable of holding said Lewis acid in close proximity to said metal component. Especially preferred is the process when the polar vinyl olefin of the formula $H_2C=CHC(O)OR^{103}$ is copolymerized with ethylene, wherein $R^{103}$ is alkyl or substituted alkyl. The Lewis acid is more preferably a cation.

Further details on (X), transition metal complexes thereof and methods of making may be found in U.S. Provisional Patent Application No. 60/264,537 (concurrently filed May 31, 2001, Ser. No. 60/264,537), which is incorporated by reference herein for all purposes as if fully set forth.

Useful olefins for the process disclosed herein include, but are not limited to one or more of ethylene, $H_2C=CH-(CH_2)_t-H$, $H_2C=CH-R^{100}-G$, norbornene, substituted norbornene, cyclopentene, or substituted cyclopentene; where t is an integer of 1 to 20, and $R^{100}$ is a covalent bond or alkylene or substituted alkylene, and G is an inert functional group. Ethylene, $H_2C=CH-(CH_2)_t-H$, and $H_2C=CH-R^{100}-G$ are more preferred, and ethylene is especially preferred. It is preferred that $R^{100}$ is a covalent bond or $-(CH_2)_q-$, G is C(O)Y, Y is $-OH$, $-NR^{101}R^{102}$, $-OR^{103}$, or $-SR^{104}$, wherein $R^{101}$ and $R^{102}$ are each independently hydrogen, hydrocarbyl or substituted hydrocarbyl, $R^{103}$ and $R^{104}$ are each hydrocarbyl or substituted hydrocarbyl, and q is an integer of 1 to 20. Especially preferred are $R^{100}$ is a covalent bond, Y is $-OR^{103}$ and $R^{103}$ is an alkyl or substituted alkyl.

Preferably ethylene is homopolymerized or copolymerized with $H_2C=CH-(CH_2)_tH$ and/or $H_2C=CH-R^{100}G$. It is more preferred that a polar olefin, particularly a polar vinyl olefin, is copolymerized with a hydrocarbon olefin or substituted hydrocarbon olefin, with hydrocarbon olefins being more preferred. Useful monomers for the copolymerization with polar vinyl olefins include ethylene and α-olefins of the formula $H_2C=CH(CH_2)_tH$, wherein t is an integer of 1 to 20, a styrene, a norbornene, cyclopentene, CO, and polar olefins, with ethylene and α-olefins being more preferred. An especially preferred olefin for copolymerization with polar vinyl olefins is ethylene.

It will be understood that not every combination of every ligand with every transition metal will polymerize every (type of) polar vinyl olefin or combination of olefins described herein. For instance, late transition metals are believed to be more efficacious for polymerization of polar olefins than are early transition metals, and the late transition metals of groups 8–11 are preferred herein. The structure of the copolymer of the polar vinyl olefin produced will also vary with the particular transition metal and ligand chosen. For example late transition metals, particularly Ni and Pd, tend to produce polymers with an unusual branching pattern, while early transition metals and metals such as iron give polymers with more "normal" branching patterns (for a description of unusual and normal branching patterns see previously incorporated U.S. Pat. No. 5,880,241). The combinations of ingredients to use in the polymerization and the products produced may be readily determined by experimentation.

It is preferred that the polymer produced by the processes herein have a degree of polymerization (average number of monomer units in a polymer molecule) of at least about 20, more preferably at least about 40, and especially preferably at least about 100.

In the polymerization processes herein, the temperature at which the polymerization is carried out is generally about −100° C. to about +200° C., preferably about −60° C. to about 170° C., and more preferably about −20° C. to about 140° C. The pressure of any of the olefins (if it is a gas) at which the polymerization is carried out is preferably atmospheric pressure to about 275 MPa.

The polymerization processes herein may be run in the presence of various liquids, particularly aprotic organic liquids. The catalyst system, monomer(s), and polymer may be soluble or insoluble in these liquids, but obviously these liquids should not prevent the polymerization from occurring. Suitable liquids include alkanes, cycloalkanes, selected halogenated hydrocarbons, and aromatic hydrocarbons. Specific useful solvents include hexane, toluene, benzene, methylene chloride, chlorobenzene, pxylene and 1,2,4-trichlorobenzene.

Cocatalysts such as alkylaluminum compounds and/or boranes and/or other Lewis acids may optionally be present in the processes herein. It is believed that the presence of certain Lewis acids may enhance the productivity of the catalyst and/or the rate of polymerization of the olefin(s). Also Lewis acids may form so-called Zwitterionic complexes which are also useful in these processes. For an explanation of Zwitterionic complexes, see U.S. patent application Ser. No. 09/871,100 (concurrently filed on May 31, 2001, Ser. No. 09/871,100), which is incorporated by reference for all purposes as if fully set forth.

One problem noted with using some polar comonomers, for example acrylate-type comonomers, under certain conditions is the tendency of these comonomers to form homopolymers. It is believed that these homopolymers arise from a "competitive" free radical-type polymerization "originating" from some free radicals which may be present or generated in the third process polymerization. Some types of polar comonomers such as acrylates are well known to readily undergo such polymerizations. These usually unwanted free radical polymerizations may be suppressed to varying extents by the presence of free radical polymerization inhibitors such as phenothiazine, but these may interfere with the desired polymerization process, or cause other problems. It has been found that the presence of alkali metal or ammonium salts, preferably alkali metal salts, of relatively noncoordinating anions retards or eliminates the formation of homopolymer of the polar comonomer (or copolymers containing only polar comonomers if more than one polar comonomer is used). Particularly preferred alkali metal cations are Li, Na and K, and Li and Na are especially preferred. Useful weakly coordinating anions include BAF, tetrakis(pentafluorophenyl)borate, $N[S(O)_2CF_3]_2^-$, tetraphenylborate, trifluoromethanesulfonate, and hexafluoroantimonate, and preferred anions are BAF, tetrakis(pentafluorophenyl)borate and $N[S(O)_2CF_3]_2^-$. A useful molar ratio of these salts to the number of moles of metal compounds present is about 10,000 to about 5 to 1.0, more preferably about 1,000 to about 50 to 1.0. These salts will preferably be used in a polymerization process in which there is a liquid phase present, for example a polymerization which is a solution or liquid suspension polymerization.

The olefin polymerizations herein may also initially be carried out in the "solid state" by, for instance, supporting the transition metal compound on a substrate such as silica or alumina, activating it if necessary with one or more cocatalysts and contacting it with the olefin(s). Alternatively, the support may first be contacted (reacted) with one or more cocatalysts (if needed) such as an alkylaluminum compound, and then contacted with an appropriate Ni compound. Another method of making a supported catalyst is to start a polymerization or at least make a transition metal complex of another olefin or oligomer of an olefin such as cyclopentene on a support such as silica or alumina. These "heterogeneous" catalysts may be used to catalyze polymerization in the gas phase or the liquid phase. By gas phase is meant that a gaseous olefin is transported to contact with the catalyst particle. For the copolymerization of polar olefins using supported catalysts, especially in a liquid medium, a preferred case is when the ligand is covalently attached to the supports, which helps prevent leaching of the transition metal complex from the support.

In all of the polymerization processes described herein, oligomers and polymers of the various olefins are made. They may range in molecular weight from oligomeric olefins, to lower molecular weight oils and waxes, to higher molecular weight polyolefins. One preferred product is a polymer with a degree of polymerization (DP) of about 10 or more, preferably about 40 or more. By "DP" is meant the average number of repeat (monomer) units in a polymer molecule.

Depending on their properties, the polymers made by the processes described herein are useful in many ways. For instance if they are thermoplastics, they may be used as molding resins, for extrusion, films, etc. If they are elastomeric, they may be used as elastomers. If they contain functionalized monomers such as acrylate esters, they are useful for other purposes, see for instance previously incorporated U.S. Pat. No. 5,880,241.

Depending on the process conditions used and the polymerization catalyst system chosen, polymers, even those made from the same monomer(s) may have varying properties. Some of the properties that may change are molecular weight and molecular weight distribution, crystallinity, melting point, and glass transition temperature. Except for molecular weight and molecular weight distribution, branching can affect all the other properties mentioned, and branching may be varied (using the same transition metal compound) using methods described in previously incorporated U.S. Pat. No. 5,880,241.

It is known that blends of distinct polymers, varying for instance in the properties listed above, may have advantageous properties compared to "single" polymers. For instance it is known that polymers with broad or bimodal molecular weight distributions may be melt processed (be shaped) more easily than narrower molecular weight distribution polymers. Thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

In such a process the transition metal containing polymerization catalyst disclosed herein can be termed the first active polymerization catalyst. Monomers useful with these catalysts are those described (and also preferred) above. A second active polymerization catalyst (and optionally one or more others) is used in conjunction with the first active polymerization catalyst. The second active polymerization catalyst may be a late transition metal catalyst, for example as described herein, in previously incorporated U.S. Pat. Nos. 5,714,556, 5,880,241, 6,060,569 and 6,174,975, and/or in U.S. Pat. No. 5,955,555 (also incorporated by reference herein for all purposes as if fully set forth). Other useful types of catalysts may also be used for the second active polymerization catalyst. For instance so-called Ziegler-Natta and/or metallocene-type catalysts may also be used. These types of catalysts are well known in the polyolefin field, see for instance *Angew. Chem., Int. Ed. Engl.*, vol. 34, p. 1143–1170 (1995), EP-A-0416815 and U.S. Pat. No. 5,198,401 for information about metallocene-type catalysts; and J. Boor Jr., *Ziegler-Natta Catalysts and Polymerizations*, Academic Press, New York, 1979 for information about Ziegler-Natta-type catalysts, all of which are hereby included by reference. Many of the useful polymerization conditions for all of these types of catalysts and the first active polymerization catalysts coincide, so conditions for the polymerizations with first and second active polymerization catalysts are easily accessible. Oftentimes the "co-catalyst" or "activator" is needed for metallocene or Ziegler-Natta-type polymerizations. In many instances the same compound, such as an alkylaluminum compound, may be used as an "activator" for some or all of these various polymerization catalysts.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, etc.

Catalyst components which include other materials such as one or more cocatalysts and/or other polymerization catalysts are also disclosed herein. For example, such a catalyst component could include the transition metal complex supported on a support such as alumina, silica, a polymer, magnesium chloride, sodium chloride, etc., with or without other components being present. It may simply be a solution of the transition metal complex, or a slurry of the transition metal complex in a liquid, with or without a support being present.

The polymers produced by this process may vary in molecular weight and/or molecular weight distribution and/or melting point and/or level of crystallinity, and/or glass transition temperature and/or other factors. For copolymers the polymers may differ in ratios of comonomers if the different polymerization catalysts polymerize the monomers present at different relative rates. The polymers produced are useful as molding and extrusion resins and in films as for packaging. They may have advantages such as improved melt processing, toughness and improved low temperature properties.

Hydrogen or other chain transfer agents such as silanes (for example trimethylsilane or triethylsilane) may be used to lower the molecular weight of polyolefin produced in the polymerization process herein. It is preferred that the amount of hydrogen present be about 0.01 to about 50 mole percent of the olefin present, preferably about 1 to about 20 mole percent. When liquid monomers (olefins) are present, one may need to experiment briefly to find the relative amounts of liquid monomers and hydrogen (as a gas). If both the hydrogen and monomer(s) are gaseous, their relative concentrations may be regulated by their partial pressures.

The polymers produced by the instant process may vary in molecular weight and/or molecular weight distribution and/or melting point and/or level of crystallinity, and/or glass transition temperature and/or other factors. The polymers produced are useful as molding and extrusion resins and in films as for packaging. They may have advantages such as improved melt processing, toughness and improved low temperature properties.

In the Examples except where noted, all pressures are gauge pressures. In the Examples, the following abbreviations are used:

| | |
|---|---|
| Am | Amyl |
| Ar | Aryl |
| BAF | B(3,5-C$_6$H$_3$—(CF$_3$)$_2$)$_4$ |
| BarF | B(C$_6$F$_5$)$_4$ |
| BHT | 2,6-Di-tert-butyl-4-methylphenol |
| BQ | 1,4-Benzoquinone |
| Bu | Butyl |
| Bu$_2$O | Dibutyl Ether |
| ca. | about |
| CB | Chlorobenzene |
| Cmpd | Compound |
| Cont'd | Continued |
| Cy | Cyclohexyl |
| E | Ethylene |
| EG | End-Group, refers to the ester group of the acrylate being located in an unsaturated end group of the ethylene copolymer |
| EGPEA | Ethylene glycol phenyl ether acrylate |
| Eoc | End-of-chain |
| Eq or Equiv | Equivalent |
| Et | Ethyl |
| Et$_2$O | Diethyl Ether |
| g | gram |
| GPC | Gel Permeation Chromatography |
| h | Hour |
| HA | Hexyl Acrylate |
| Hex | Hexyl |
| IC | In-Chain, refers to the ester group of the acrylate being bound to the main-chain of the ethylene copolymer |
| Incorp | Incorporation |
| i-Pr | iso-Propyl |
| LA | Lewis Acid |
| LAIC | Lewis Acid Interaction Cone |
| M.W. | Molecular Weight |
| MA | Methyl Acrylate |
| Me | Methyl |
| MeOH | Methanol |
| MI | Melt Index |
| mL | Milliliter |
| mmol | Millimole |
| M$_n$ | Number Average Molecular Weight |
| mol | Mole |
| M$_p$ | Peak Average Molecular Weight |
| M$_w$ | Weight Average Molecular Weight |
| Nd | Not Determined |
| NMR | Nuclear Magnetic Resonance |
| p | Para |
| PDI | Polydispersity; M$_w$ divided by M$_n$ |
| PE | Polyethylene |
| Ph | Phenyl |
| PPA | 2,2,3,3,3,-Pentafluoropropyl acrylate |
| Press | Pressure |
| RI | Refractive Index |
| RT | Room Temperature |
| t-Bu | tert-Butyl |
| TCB | 1,2,4-Trichlorobenzene |
| Temp | Temperature |
| THA | 3,5,5-Trimethylhexyl Acrylate |
| THF | Tetrahydrofuran |
| TO | Number of turnovers per metal center = (moles monomer consumed, as determined by the weight of the isolated polymer or oligomers) divided by (moles catalyst) |
| Total Me | Total number of methyl groups per 1000 methylene groups as determined by $^1$H or $^{13}$C NMR analysis |
| Uv | Ultraviolet |

General Information Regarding Total Me Analysis

Total methyls per 1000 CH$_2$ are measured using different NMR resonances in $^1$H and $^{13}$C NMR spectra. Because of accidental overlaps of peaks and different methods of correcting the calculations, the values measured by $^1$H and $^{13}$C NMR spectroscopy will not be exactly the same, but they will be close, normally within 10–20% at low levels of acrylate comonomer. In $^{13}$C NMR spectra, the total methyls per 1000 CH$_2$ are the sums of the 1B$_1$, 1B$_2$, 1B$_3$, and 1B$_{4+}$, EOC resonances per 1000 CH$_2$, where the CH$_2$'s do not include the CH$_2$'s in the alcohol portions of the ester group. The total methyls measured by $^{13}$C NMR spectroscopy do not include the minor amounts of methyls from the methyl vinyl ends nor the methyls in the alcohol portion of the ester group. In $^1$H NMR spectra, the total methyls are measured from the integration of the resonances from 0.6 to 1.08 ppm and the CH$_2$'s are determined from the integral of the region from 1.08 to 2.49 ppm. It is assumed that there is 1 methine for every methyl group, and ⅓ of the methyl integral is subtracted from the methylene integral to remove the methine contribution. The methyl and methylene integrals are also usually corrected to exclude the values of the methyls and methylenes in the alcohol portion of the ester group, if this is practical. Because of the low levels of incorporation, this is usually a minor correction.

General Information Regarding Molecular Weight Analysis

GPC molecular weights are reported versus polystyrene standards. Unless noted otherwise, GPC's were run with RI detection at a flow rate of 1 mL/min at 135° C. with a run time of 30 min. Two columns were used: AT-806MS and WA/P/N 34200. A Waters RI detector was used and the solvent was TCB with 5 grams of BHT per gallon. Dual UV/RI detection GPC was run in THF at RT using a Waters 2690 separation module with a Waters 2410 RI detector and a Waters 2487 dual absorbance detector. Two Shodex columns, KF-806M, were used along with one guard column, KF-G.

In addition to GPC, molecular weight information was at times determined by $^1$H NMR spectroscopy (olefin end group analysis) and by melt index measurements (g/10 min at 190° C.).

General Procedure A for Ethylene Polymerizations and Copolymerizations

In a nitrogen-filled drybox, a 40 mL glass insert was loaded with the nickel compound and, optionally, a Lewis acid (e.g., BPh$_3$ or B(C$_6$F$_5$)$_3$) and borate (e.g., NaBAF or LiBArF) and any other specified cocatalysts and other additives. Next, the solvent was added to the glass insert followed by the addition of any co-solvents and then comonomers. The insert was greased and capped. The glass insert was then loaded in a pressure tube inside the drybox. The pressure tube was then sealed, brought outside of the drybox, connected to the pressure reactor, placed under the desired ethylene pressure and shaken mechanically. After the stated reaction time, the ethylene pressure was released and the glass insert was removed from the pressure tube. The polymer was precipitated by the addition of MeOH (~20 mL). The polymer was then collected on a frit and rinsed with MeOH and, optionally, acetone. The polymer was transferred to a pre-weighed vial and dried under vacuum overnight. The polymer yield and characterization were then obtained.

EXAMPLES

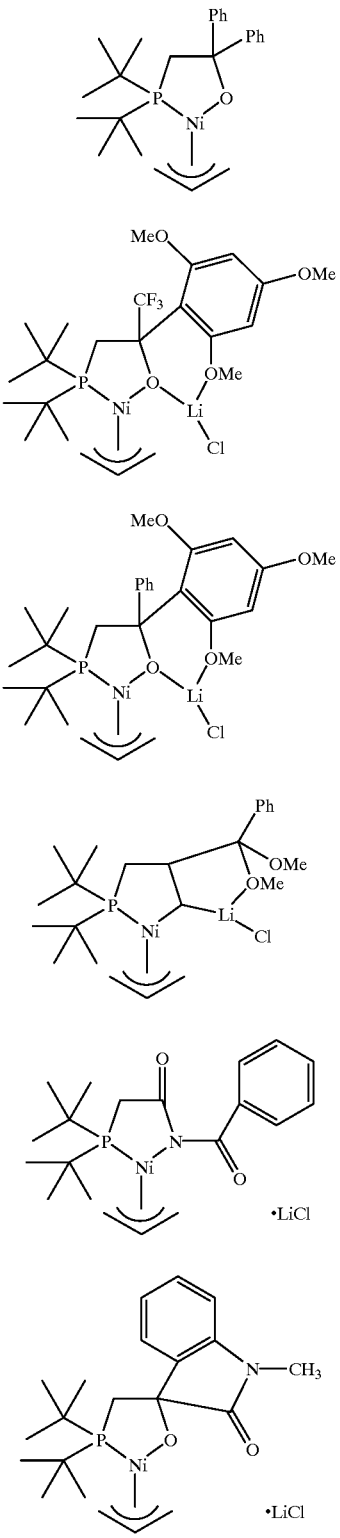

Synthesis of Catalyst 1

A 100-mL round-bottomed flask was charged with 292 mg (1.60 mmol) of benzophenone dissolved in ca. 15 mL THF. Then (tBu)$_2$P—CH$_2$Li (266 mg, 1.60 mmol) dissolved in ca.15 mL THF was added. The solution turned from colorless to dark blue. It was stirred for one hour after which time, a solution of [Ni(C$_3$H$_5$)Cl]$_2$ (217 mg, 0.80 mmol) in 15 mL THF was added. It was stirred for an additional 1 h and the solvent removed. The residue was extracted with hexane and toluene and the solvent removed. The residue was washed with small amounts of hexane and dried. The yield was 395 mg (71%). $^1$HNMR (CD$_2$Cl$_2$, 23° C., 300 MHz) d 8.2–7.9 (m, 4H, Ar); 7.4–6.9 (m, 6H, Ar); 5.10 (m, 1H); 4.26 (brs, 1H); 3.25 (dd, J=14 Hz, J=5 Hz, 1H), 2.80 (m, 2H), 2.24 (brs, 1H), 1.16 (d, J=13 Hz, 1H), 0.97 (d, JP-H=13 Hz, 9H); 0.80 (d, JP-H=13 Hz). $^{31}$PNMR (CD$_2$Cl$_2$, 23° C.,): d 84.0. $^{13}$CNMR (CD$_2$Cl$_2$, 23° C., 75 MHz) d 156.1 (s); Ar C—H signals overlapping with C$_6$D$_6$ signal; 127.2 (s); 125.7 (d, JP-C=6 Hz); 109.3 (d, JC-H=157 Hz); 86.7 (d, JP-C=10 Hz); 69.1 (m, JP-C=22 Hz); 41.2 (dt, JP-C=25 Hz, JC-H=127 Hz); 37.6 (m, JP-C=6 Hz); 33.8 (m); 29.9 (q, JC-H=124 Hz). A single red-orange crystal was grown from CH$_2$Cl$_2$/hexane at ambient temperature, and X-ray diffraction data confirmed the structure.

Synthesis of Catalyst 2

A 100 mL RB flask was charged with 217 mg(0.82 mmol) of 2,2,2-trifluoro-2',4',6'-trimethoxyacetophenone dissolved in ca. 10–15 mL THF. Then (tBu)$_2$P—CH$_2$Li (136 mg, 0.82 mmol) dissolved in ca. 10–15 mL THF was added. The initially purple solution (color came from traces impurities in starting ketone) turned clear yellow. It was stirred for one h after which time, a solution of [Ni(C$_3$H$_5$)Cl]$_2$ (111 mg, 0.41 mmol) in 10–15 mL THF was added. It was stirred for an additional one h and the solvent removed. The residue was washed with hexane and dried in vacuo to yield 362 mg (78%). Key NMR signals (incomplete): $^1$HNMR (CD$_2$Cl$_2$, 23° C., 300 MHz) δ6.5–6.2 (brm, 2H, Ar); 5.3 (brm, 1H), 4.8 (brs, 1H); 4.1 (brs, 2H); 3.8 (brs, 9H); 3.7–2.0 (brm); 2.0–0.8 (brm, $^t$Bu signals). Two isomers (50:50) by $^{31}$PNMR (CD$_2$Cl$_2$, 23° C., 300 MHz): δ81.4; 80.2. $^{13}$CNMR (CD$_2$Cl$_2$, 23° C., 125 MHz): δ161.3 (s); ca. 112 (brs); ca. 94.0 (brm, J=158 Hz); 93.2 (br); ca. 86; 68.1; 58.4; 56.3; 55.6. A single red-orange crystal was grown from CH$_2$Cl$_2$/hexane at ambient temperature, and the structure confirmed by X-ray diffraction. In solid state the complex contains one equivalent of LiCl. It is believed that it exists as dimer bridged by LiCl.

Synthesis of Catalyst 3

A 200 mL RB flask was charged with 300 mg (1.10 mmol) of 2,4,6-trimethoxybenzophenone dissolved in ca. 20 mL THF. Then (tBu)$_2$P—CH$_2$Li (183 mg, 1.10 mmol) dissolved in ca. 20 mL THF was added. It was stirred for one h, after which time, a solution of [Ni(C$_3$H$_5$)Cl]$_2$ (149 mg, 0.55 mmol) in THF (ca. 20 mL) was added. It was stirred for an additional one h and the solvent removed. The residue was washed with hexane and dried in vacuo to yield 664 mg product. Key NMR signals (incomplete): $^1$HNMR (CD$_2$Cl$_2$, 23° C., 300 MHz) δ7.64 (brs, 1H, Ar); 7.51 (brs, 1H, Ar); 7.14 (brt, 2H, Ar); 7.00 (brt, 1H, Ar); 6.14 (s, 2H); 5.28 (m, 1H); 5.0–4.5 (brm, 2H); 3.67 (s, 3H, OCH3); 3.64 (s, 6H, OCH$_3$); 3.26 (brs, 1H); 2.87 (dd, 1H, J=14 Hz, J=5 Hz); 2.8–2.4 (brm, 2H); 1.7–0.7 (brm, 18H, tBu). Two isomers (50:50) by $^{31}$PNMR (CD$_2$Cl$_2$, 23° C., 75 MHz): δ79.0; 78.2. $^{13}$CNMR (CD$_2$Cl$_2$, 23° C., 125 MHz): δ167.9 (d, J$_{P-C}$=4.5

Hz); 159.9 (s); 158.5 (brs); 154.4 (brs); 127.6 (dd, $J_{C-H}$=158 Hz, J=7.5 Hz); 126.1 (dt); 125.7 (dt, J=150 Hz); 111.0 (brd); 95.0 (dd, $J_{C-H}$=159 Hz, J=4.7 Hz); 87.2 (brs); 67.0 (brdt, $J_{P-C}$=22 Hz); 57.7 (q, $J_{C-H}$=145 Hz); 55.6 (q, $J_{C-H}$=144 Hz); ca. 40.0 (brs); 39.7 (dt, $J_{P-C}$=25 Hz); 35.3 (d, $J_{P-C}$=18 Hz); 33.7 (d, $J_{P-C}$=16 Hz); 30.0 (brq, $J_{C-H}$=127 Hz). A single red-orange crystal was grown from $CH_2Cl_2$/hexane at ambient temperature, and an X-ray diffraction confirmed the structure. In solid state the complex contained one equivalent of LiCl. It is believed that it existed as a dimer bridged by LiCl.

Synthesis of Catalyst 4

A 200 mL RB flask was charged with 300 mg(1.17 mmol) of 2,2-dimethoxy-2-phenylacetophenone dissolved in ca. 20 mL THF. Then $(tBu)_2P-CH_2Li$ (195 mg, 1.17 mmol) dissolved in ca. 20 mL THF was added. It was stirred for one h, after which time a solution of $[Ni(C_3H_5)Cl]_2$ (158 mg, 0.59 mmol) in THF (ca. 20 mL) was added. It was stirred for an additional h and the solvent removed. The residue was washed with hexane and dried in vacuo to yield 438 mg (67%). Two isomers (50:50) by $^{31}$PNMR ($CD_2Cl_2$, 23° C., 300 MHz): δ82.1 (s) and δ81.5 (s). A single red-orange crystal was grown from $CH_2Cl_2$/hexane at ambient temperature, and X-ray diffraction data confirmed the structure. In solid state the complex contained one equivalent of LiCl. It is believed that it existed as a dimer bridged by LiCl.

Synthesis of Catalyst 5

In a dry box, benzoylisocyanate (0.1966 g, 1.336 mmole) was dissolved in 20 mL THF in a 100 mL RB flask. The solution was cooled to ca. −30° C. in a freezer. $(t.-Bu)_2PCH_2Li$ (0.2220 g, 1.336 mmole) was added to the above cold solution under stirring. The mixture turned dark red. It was allowed to stir at RT for 4 h. The solution was then evaporated to dryness. To the ligand precursor (ca. 1.300 mmole) was added 20 mL THF. Under stirring, nickel allyl chloride dimer (0.1760 g, 0.6500 mmole) was added to the mixture. The solution became dark red. It was allowed to stir at RT for 2 h. Solvent was evaporated. Toluene (ca. 8 mL) was added to the brick red residue. Upon brief stirring, large excess of pentane was added. The resulting solid was filtered, followed by 3×pentane wash, and dried in vacuo. Pale orange solid (0.4223 g, 2%) was obtained.

Synthesis of Catalyst 6

In a drybox, 0.485 g (3.01 mmole) 1-methylisatin and 20 mL THF were combined. The orange solution was cooled at 30° C. for 45 min. Then 0.500 g (3.01 mmole) $(t-Bu)_2PCH_2Li$ was added. The reaction mixture turned purple and it was stirred at RT for 1 h. To the reaction mixture was added 0.407 g (1.505 mmole) nickel allyl chloride dimer. The red solution was stirred at RT for 3 h. The reaction mixture was then evaporated under full vacuum overnight. To the residue was added 20 mL toluene. The solution was filtered through Celite®, followed by 3×10 mL toluene wash. The filtrate was evaporated under full vacuum. Final weight of the dark brown solid was 1.463 g.

Examples 1–7

The catalyst systems used in Examples 1–7 are shown above. These structures illustrate just one of the possible products and binding modes that may have formed during the synthesis of the ligand and the subsequent synthesis of the nickel compound and are not meant to be restrictive. Table 1 shows that Lewis acid binding catalysts 2, 3, 4 are more active for ethylene/hexyl acrylate (HA) copolymerization, compared to catalyst 1. Table 1A shows examples of ethylene/hexyl acrylate copolymerization using Lewis acid binding catalysts 2, 5 and 6, performed using General Polymerization Procedure A above.

TABLE 1

E/HA Copolymerization Using 0.02 mmole Catalyst, 40 equiv $B(C_6F_5)_3$, 20 equiv $LiB(C_6F_5)_4$, 8 mL TCB, 2 mL HA, at 120° C. under 6.9 MPa Ethylene for 18 h

| Ex | Catalyst | Yield (g) | #Me/ 1000 $CH_2$ | Mole % Comonomer | m.p. (° C.) ($\Delta H_f$) | Mw/PDI |
|---|---|---|---|---|---|---|
| 1 | 1 | 0.461 | 9 | 0.41 ($^{13}$C) 0.20 IC 0.21 EG | 125 (186.6) | 22,311/10.8 |
| 2 | 2 | 3.998 | 10 | 0.54 ($^{13}$C) 0.25 IC 0.29 EG | 124 (209.5) | 3,567/2.2 |
| 3 | 3 | 1.253 | 13 | 0.53 ($^{13}$C) 0.25 IC 0.28 EG | 122 (190.6) | 11,123/10.8 |
| 4 | 4 | 1.075 | 19 | 0.38 ($^{13}$C) 0.19 IC 0.19 EG | 112 (191.2) | 1,405/1.8 |

TABLE 1A

E/HA Copolymerization Using 0.02 mmole Catalyst, 40 equiv $B(C_6F_5)_3$, 8 mL TCB, 2 mL HA, at 120° C. under 6.9 MPa Ethylene for 18 h

| Ex | Cat | Sm (OTf)$_3$ | LiB ($C_6F_5$)$_4$ | Yield (g) | #Me/ 1000 $CH_2$ | Mole % Comonomer | m.p. (° C.) ($\Delta H_f$) | Mw/PDI |
|---|---|---|---|---|---|---|---|---|
| 5 | 2 | 1 eq | 0 eq | 1.429 | 28 | 0.6 | 118 (96.0) | 9,859/8.8 |
| 6 | 5 | 0 eq | 0 eq | 0.216 | 28 | 0.8 | 111 (158.3) 97 | Bimodal- First 497,946/2.3 Second MP = 887 |
| 7 | 6 | 0 eq | 20 eq | 0.395 | / | / | / | / |

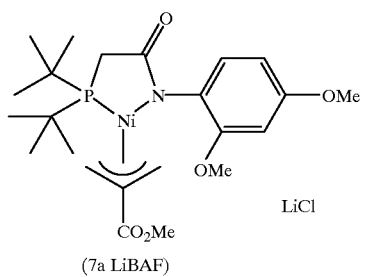

(7a LiBAF)

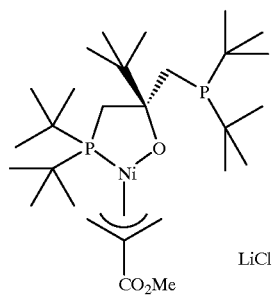

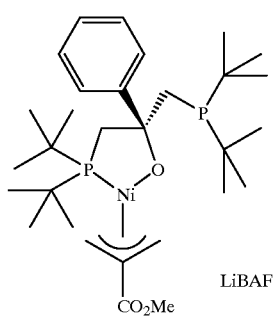

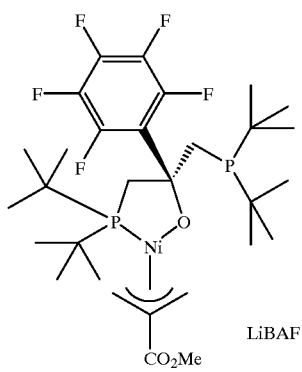

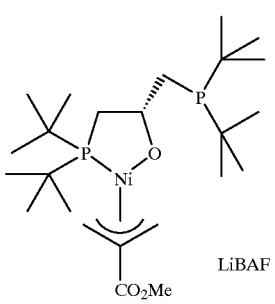

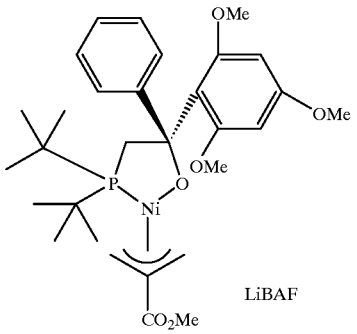

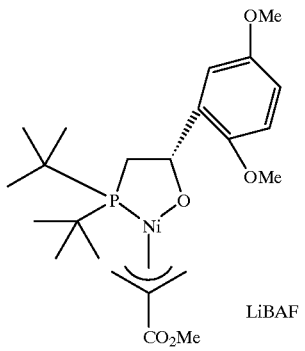

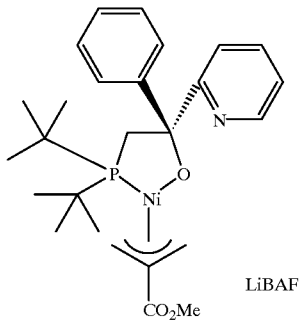

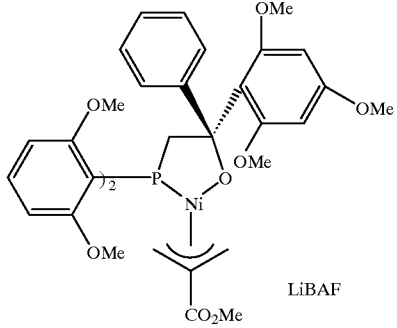

Synthesis of Catalysts 7–15

Catalyst 15: 2,6-Bis-dimethoxyphenyllithium was prepared from 14.18 g (0.103 mole) of 1,3-dimethoxybenzene, 77 mL of a 1.6 M solution of BuLi in hexanes and 0.23 mL of N,N,N',N'-tetramethylethylenediamine in dry diethyl ether (72 mL). Dichloromethylphosphine (5.0 g, 0.04276 mole) was added at 0° C., and the reaction mixture was stirred at room temperature overnight. Methanol (20 mL) was added, and the mixture was concentrated to about half its original volume under reduced pressure. The resulting white precipitates were filtered and were recrystallized from methanol to give white crystals of bis-(2,6-dimethoxyphenyl)(methyl)phosphine with 48% yield (6.6 g) and melting point at 112.33° C. $^1$H NMR (CDCl$_3$) δ1.75 (s (broad), 3H, Me-P), 3.55 (s, 12H, Me-O), 6.4–7.2 (m, 6H, aromatic protons); $^{31}$P NMR (CDCl$_3$) δ–51.5 ppm. LS/MS: found m/w is 321, calculated m/w is 321. Anal. found: C 64.30%; H 6.45%; calculated for C$_{17}$H$_{22}$O$_4$P: C 63.49%; H 6.85%.

Bis-(2,6-dimethoxyphenyl)phosphino]methyllithium(2,6-MeO-Ph)$_2$P—CH$_2$—Li) (0.33 g, 0.001 mole) was prepared from a 7 mL THF solution of equi-molar amounts of bis-(2,6-dimethoxyphenyl)(methyl)phosphine and a 1.6 M solution of butyllithium in hexanes with a catalytic amount of TMEDA added. 2,4,6-Trimethoxy-benzophenone (0.30 g, 0.001 mole) in 3 mL of THF was added to the reaction mixture, which was then stirred for 12 hours. Next, 0.24 g (0.0005 mole) of 2-methoxycarbonylallyl nickel bromide dimer [(CH$_2$=C(CO$_2$Me)CH$_2$)Ni(μ-Br)]$_2$ and 0.89 g (0.001 mole) of NaBAF in 4 mL of THF was added into reaction mixture, which was stirred overnight. The next day, the solvent was pumped off and the residue was redissolved in diethyl ether. The solution was filtered through Celite®, and solvent was removed under vacuum. Viscous brown product (1.11 g) was obtained. $^{31}$p NMR (CD$_2$Cl$_2$): one major peak at 22.5 ppm.

Synthesis was in a fashion analogous to that reported for catalysts 7–14 above, except that (t-Bu)$_2$PCH$_2$Li was employed as the base and different electrophiles were employed. The electrophiles employed and compound characterization are reported in Table 2A below:

TABLE 2A

| Catalyst | Electrophile | $^{31}$P NMR (C$_6$D$_6$) of Ligand (ppm) [a,c] | $^{31}$P NMR (CD$_2$Cl$_2$) of Cmpd (ppm) [b,c] |
|---|---|---|---|
| 7a | 2,4-Dimethoxy-phenylisocyanate | 6.7; 0.0 | 60.6 (major); 62.1 (minor) |

TABLE 2A-continued

| Catalyst | Electrophile | $^{31}$P NMR (C$_6$D$_6$) of Ligand (ppm) [a,c] | $^{31}$P NMR (CD$_2$Cl$_2$) of Cmpd (ppm) [b,c] |
|---|---|---|---|
| 8 | Methyl Trimethyl acetate | 12.6; 7.0 | 78.9 (major); 47.7 & 47.2 (minor) |
| 9 | Phenyl Benzoate | 20.2 | 74.6 (major) |
| 10 | Methyl Penta-fluoro-benzoate | 38.7–36.3; 31.5; 15.4; 12.7 | 71.7 (major) |
| 11 | 1-Formyl-piperidine | Not acquired | 75.4 (major) |
| 12 | 2,4,6-Trimethoxy-benzo-phenone | 21.8; 14.8 | 82.9; 80.3 |
| 13 | 2,5-Dimethoxy-benzaldehyde | 21.4 | 80.6 (major) |
| 14 | 2-Benzoyl pyridine | 14.7 | 80.3; 47.2 |

[a] This is the phosphorus NMR characterization of the isolated ligand prior to reaction with the nickel precursor.
[b] This is the phosphorus NMR characterization of the nickel compound.
[c] In some cases, additional minor resonances were present in the phosphorus NMR spectra.

Examples 8–51

Examples 8–51 are listed in Table 2 below. These structures above illustrate just one of the possible products and binding modes that may have formed during the synthesis of the ligand and the subsequent synthesis of the nickel compound and are not meant to be restrictive. The polymerizations were carried out according to General Polymerization Procedure A. Varying amounts of acrylate homopolymer are present in some of the isolated polymers. In Table 1A, the yield of the polymer is reported in grams and includes the yield of the dominant ethylene/acrylate copolymer as well as the yield of any acrylate homopolymer that was formed. Molecular weights were determined by GPC, unless indicated otherwise. Mole percent acrylate incorporation and total Me were determined by $^1$H NMR spectroscopy, unless indicated otherwise. Mole percent acrylate incorporation is typically predominantly IC, unless indicated otherwise. The LiB(C$_6$F$_5$)$_4$ used (LiBArF) included 2.5 equiv of Et$_2$O.

TABLE 2

Ethylene/Acrylate Copolymerizations

| EX | Catalyst (mmol) | Acrylate mL (Solvent mL) | B(C$_6$F$_5$)$_3$ (Borate) | Press psi | Temp ° C. | Yield g | Acrylate Incorp. mol % | M.W. | Total Me |
|---|---|---|---|---|---|---|---|---|---|
| 8 | 7 (0.022) | EGPEA 1 (TCB 9) | 18 equiv (NaBAF 9 equiv) | 1000 | 120 | 5.60 | 0.50 ~.25 IC ~.25 EG | M$_p$ = 3,837; M$_w$ = 4,459; M$_n$ = 1,507; PDI = 2.96 | 18.1 |
| 9 | 7 (0.005) | EGPEA 1 (TCB 9) | 80 equiv (NaBAF 5 equiv) | 1000 | 120 | 0.134 | 0.7 0.4 IC 0.3 EG | M$_n$ ($^1$H) = 3,492 | 15.3 |
| 10 | 7 (0.005) | EGPEA 1 (TCB 9) | 80 equiv (NaBAF 40 equiv) | 1000 | 120 | 1.35 | 0.7 0.4 IC 0.3 EG | M$_p$ = 4,137; M$_w$ = 4,233; M$_n$ = 1,712; PDI = 2.47 | 16.1 |
| 11 | 7 (0.005) | EGPEA 1 (p-Xylene 9) | 80 equiv (LiBArF 5 equiv) | 1000 | 120 | 0.131 | 0.7 0.4 IC 0.3 EG | M$_n$ ($^1$H) = 2,559 | 16.9 |
| 12 | 7 (0.005) | EGPEA 1 (p-Xylene 9) | 80 equiv (LiBArF 40 equiv) | 1000 | 120 | 0.053 | 0.9 | M$_n$ ($^1$H) = 12,600 | 24.6 |
| 13 | 7a (0.02) | EGPEA 2 (p-Xylene 8) | 20 equiv (NaBAF 10 equiv) | 1000 | 120 | 8.06 | 1.5 0.7 IC 0.8 EG | M$_p$ = 3,098; M$_w$ = 3,461; M$_n$ = 1,122; PDI = 3.09 | 22.3 |

TABLE 2-continued

Ethylene/Acrylate Copolymerizations

| EX | Catalyst (mmol) | Acrylate mL (Solvent mL) | B(C$_6$F$_5$)$_3$ (Borate) | Press psi | Temp °C | Yield g | Acrylate Incorp. mol % | M.W. | Total Me |
|---|---|---|---|---|---|---|---|---|---|
| 14 | 7a (0.02) | EGPEA 1 (p-Xylene 9) | 20 equiv (NaBAF 10 equiv) | 500 | 60 | 2.43 | 0.6 0.3 IC 0.3 EG | M$_p$ = 11,050; M$_w$ = 11,523; M$_n$ = 5,109; PDI = 2.26 | 6.3 |
| 15 | 7a (0.004) | EGPEA 1 (p-Xylene 9) | 100 equiv (NaBAF 50 equiv) | 500 | 60 | 0.64 | 0.5 0.3 IC 0.2 EG | M$_p$ = 13,148; M$_w$ = 14,087; M$_n$ = 6,487; PDI = 2.17 | 7.1 |
| 16 | 7a (0.02) | EGPEA 1 (p-Xylene 9) | 20 equiv (NaBAF 10 equiv) | 150 | 60 | 0.09 | 1.4 0.7 IC 0.7 EG | M$_p$ = 5,447; M$_w$ = 8,088; M$_n$ = 3,454; PDI = 2.17 | 13.3 |
| 17 | 8 (0.02) | None (TCB 10) | 10 equiv (None) | 150 | 25 | 9.90 | — | M$_p$ = 8,676; M$_w$ = 10,088; M$_n$ = 3,013; PDI = 3.35 | 26.0 |
| 18 | 8 (0.02) | EGPEA 2 (TCB 8) | 40 equiv (None) | 1000 | 120 | 0.70 | 1.6 1.1 IC 0.4 EG | M$_p$ = 1,355; M$_w$ = 2,788; M$_n$ = 1,136; PDI = 2.45 | 17.6 |
| 19 | 8 (0.02) | EGPEA 1 (p-Xylene 9) | 20 equiv (NaBAF 10 equiv) | 1000 | 120 | 11.93 | 0.3 0.2 IC 0.1 EG | M$_p$ = 1,248; M$_w$ = 1,857; M$_n$ = 733; PDI = 2.53 | 27.1 |
| 20 | 8 (0.02) | EGPEA 1 (p-Xylene 9) | 20 equiv (NaBAF 10 equiv) | 500 | 60 | 2.15 | 0.4 0.2 IC 0.2 EG | M$_p$ = 3,738; M$_w$ = 4,285; M$_n$ = 1,882; PDI = 2.28 | 15.9 |
| 21 | 8 (0.02) | EGPEA 2 (p-Xylene 8) | 20 equiv (NaBAF 10 equiv) | 1000 | 120 | 3.15 | 1.7 1.0 IC 0.7 EG | M$_p$ = 1,389; M$_w$ = 1,897; M$_n$ = 799; PDI = 2.37 | 28.7 |
| 22 | 8 (0.004) | EGPEA 1 (p-Xylene 9) | 100 equiv (NaBAF 50 equiv) | 500 | 60 | 0.76 | 0.3 0.2 IC 0.1 EG | M$_p$ = 4,663; M$_w$ = 5,185; M$_n$ = 2,408; PDI = 2.15 | 14.8 |
| 23 | 8 (0.02) | EGPEA 2 (p-Xylene 8) | 20 equiv (NaBAF 10 equiv) | 500 | 60 | 2.05 | 0.6 0.3 IC 0.3 EG | M$_p$ = 3,502; M$_w$ = 4,226; M$_n$ = 1,177; PDI = 2.38 | 11.0 |
| 24 | 8 (0.02) | EGPEA 1 (p-Xylene 9) | 20 equiv (NaBAF 10 equiv) | 150 | 60 | 0.51 | 1.4 0.7 IC 0.7 EG | M$_p$ = 2,997; M$_w$ = 5,001; M$_n$ = 1,755; PDI = 2.85 | 21.3 |
| 25 | 8 (0.004) | EGPEA 1 (p-Xylene 9) | 20 equiv (NaBAF 10 equiv) | 150 | 60 | 0.076 | 1.3 0.6 IC 0.7 EG | M$_p$ = 2,820; M$_w$ = 4,856; M$_n$ = 1,934; PDI = 2.51 | 17.2 |
| 26 | 9 (0.02) | EGPEA 2 (p-Xylene 8) | 20 equiv (NaBAF 10 equiv) | 1000 | 120 | 2.26 | 2.1 1.3 IC 0.8 EG | M$_p$ = 1,827; M$_w$ = 1,925; M$_n$ = 863; PDI = 2.23 | 28.1 |
| 27 | 9 (0.02) | EGPEA 1 (p-Xylene 9) | 20 equiv (NaBAF 10 equiv) | 500 | 60 | 2.30 | 0.5 0.3 IC 0.2 EG | M$_p$ = 4,366; M$_w$ = 4,906; M$_n$ = 1,823; PDI = 2.69 | 18.1 |
| 28 | 9 (0.004) | EGPEA 1 (p-Xylene 9) | 100 equiv (NaBAF 50 equiv) | 500 | 60 | 0.53 | 0.5 0.3 IC 0.2 EG | M$_p$ = 4,976; M$_w$ = 6,139; M$_n$ = 2,635; PDI = 2.17 | 13.2 |
| 29 | 9 (0.02) | EGPEA 2 (p-Xylene 8) | 20 equiv (NaBAF 10 equiv) | 500 | 60 | 1.05 | 0.7 0.4 IC 0.3 EG | M$_p$ = 3,692; M$_w$ = 4,659; M$_n$ = 1,890; PDI = 2.47 | 10.4 |
| 30 | 9 (0.02) | EGPEA 1 (p-Xylene 9) | 20 equiv (NaBAF 10 equiv) | 150 | 60 | 0.29 | 1.7 1.0 IC 0.7 EG | M$_p$ = 3,312; M$_w$ = 5,176; M$_n$ = 2,056; PDI = 2.52 | 20.0 |
| 31 | 9 (0.004) | EGPEA 1 (p-Xylene 9) | 20 equiv (NaBAF 10 equiv) | 150 | 60 | 0.067 | 1.5 0.8 IC 0.7 EG | M$_p$ = 3,444; M$_w$ = 5,374; M$_n$ = 2,120; PDI = 2.53 | 19.4 |

TABLE 2-continued

Ethylene/Acrylate Copolymerizations

| EX | Catalyst (mmol) | Acrylate mL (Solvent mL) | B(C$_6$F$_5$)$_3$ (Borate) | Press psi | Temp °C. | Yield g | Acrylate Incorp. mol % | M.W. | Total Me |
|---|---|---|---|---|---|---|---|---|---|
| 32 | 10 (0.02) | EGPEA 2 (p-Xylene 8) | 20 equiv (NaBAF 10 equiv) | 1000 | 120 | 2.58 | 2.5 1.4 IC 1.1 EG | M$_p$ = 1,678; M$_w$ = 2,683; M$_n$ = 1,002; PDI = 2.68 | 33.4 |
| 33 | 10 (0.02) | EGPEA 1 (p-Xylene 9) | 20 equiv (NaBAF 10 equiv) | 500 | 60 | 0.40 | 0.6 0.4 IC 0.2 EG | Bimodal: M$_p$ = 6,027; M$_w$ = 10,310; M$_n$ = 6,665; PDI = 1.55 M$_p$ = 943; M$_w$ = 5,879; M$_n$ = 1,231; PDI = 4.78 | 12.0 |
| 34 | 11 (0.022) | EGPEA 1 (TCB 9) | 18 equiv (NaBAF 9 equiv) | 1000 | 120 | 0.50 | 0.50 IC & EG | M$_p$ = 540; M$_w$ = 1,264; M$_n$ = 602; PDI = 2.10 | 34.4 |
| 35 | 12 (0.02) | EGPEA 1 (TCB 9) | 20 equiv (NaBAF 10 equiv) | 1000 | 100 | 3.34 | 0.4 0.2 IC 0.2 EG | M$_p$ = 3,085; M$_w$ = 4,966; M$_n$ = 1,436; PDI = 3.46 | 33.4 |
| 36 | 12 (0.02) | HA 1 (p-Xylene 9) | 40 equiv (NaBAF 10 equiv) | 1000 | 120 | 1.40 | 0.8 0.6 IC 0.2 EG | M$_p$ = 1,973; M$_w$ = 3,527; M$_n$ = 1,312; PDI = 2.69 | 20.4 |
| 37 | 12 (0.02) | HA 1 (p-xylene 9) | 40 equiv (LiBArF 10 equiv) | 1000 | 120 | 3.32 | Nd | M$_p$ = 408; M$_w$ = 2,087; M$_n$ = 369; PDI = 5.65 | Nd |
| 38 | 12 (0.02) | HA 1 (p-Xylene 9) | 20 equiv (LiBArF 10 equiv) | 1000 | 120 | 0.50 | 0.4 0.3 IC 0.1 EG | M$_p$ = 585; M$_w$ = 3,859; M$_n$ = 995; PDI =3.88 | 15.1 |
| 39 | 12 (0.02) | HA 1 (p-Xylene 9) | 20 equiv (LiBArF 10 equiv) | 1000 | 80 | 0.87 | 0.3 IC & EG | M$_p$ = 4,746; M$_w$ = 9,440; M$_n$ = 2,917; PDI = 3.24 | 8.1 |
| 40 | 12 (0.005) | EGPEA 1 (TCB 9) | 80 equiv (NaBAF 5 equiv) | 1000 | 120 | 0.22 | 0.7 0.4 IC 0.3 EG | M$_p$ = 3,204; M$_w$ = 4,082; M$_n$ = 1,437; PDI = 2.84 | 12.2 |
| 41 | 12 (0.005) | EGPEA 1 (TCB 9) | 80 equiv (NaBAF 40 equiv) | 1000 | 120 | 9.70 | 0 | M$_p$ = 2,151; M$_w$ = 2,685; M$_n$ = 944; PDI = 2.84 | Nd |
| 42 | 12 (0.005) | EGPEA 1 (p-Xylene 9) | 80 equiv (LiBArF 5 equiv) | 1000 | 120 | 0.11 | 0.4 IC & EG | Bimodal: M$_p$ = 3,598; M$_w$ = 8,375; M$_n$ = 4,985; PDI = 1.68 M$_p$ = 585; M$_w$ = 4,884; M = 1069; PDI = 4.57 | 14.8 |
| 43 | 12 (0.005) | EGPEA 1 (p-Xylene 9) | 80 equiv (LiBArF 40 equiv) | 1000 | 120 | 0.050 | 1.4 0.9 IC 0.5 EG | M$_p$ = 4,865; M$_w$ = 5,118; M$_n$ = 1,255; PDI = 4.08 | 17.4 |
| 44 | 12 (0.02) | EGPEA 2 (p-Xylene 8) | 20 equiv (NaBAF 10 equiv) | 1000 | 120 | 3.98 | 0.9 0.5 IC 0.4 EG | M$_p$ = 1,965; M$_w$ = 2,793; M$_n$ = 945; PDI = 2.96 | 17.6 |
| 45 | 13 (0.02) | EGPEA 2 (p-Xylene 8) | 20 equiv (NaBAF 10 equiv) | 1000 | 120 | 0.77 | 2.1 1.5 IC 0.6 EG | M$_p$ = 570; M$_w$ = 1,187; M$_n$ = 536; PDI = 2.21 | 39.7 |
| 46 | 13 (0.02) | EGPEA 2 (p-Xylene 8) | 20 equiv (NaBAF 10 equiv) | 500 | 60 | 0.98 | 0.4 0.3 IC 0.1 EG | M$_p$ = 755; M$_w$ = 1,407; M$_n$ = 589; PDI = 2.39 | 28.3 |

TABLE 2-continued

Ethylene/Acrylate Copolymerizations

| EX | Catalyst (mmol) | Acrylate mL (Solvent mL) | $B(C_6F_5)_3$ (Borate) | Press psi | Temp °C | Yield g | Acrylate Incorp. mol % | M.W. | Total Me |
|---|---|---|---|---|---|---|---|---|---|
| 47 | 14 (0.02) | EGPEA 2 (p-Xylene 8) | 20 equiv (NaBAF 10 equiv) | 1000 | 120 | 1.93 | 9.4[a] IC & EG | $M_p$ = 6,284; $M_w$ = 6,362; $M_n$ = 1,579; PDI = 4.03 | 31.5 |
| 48 | 14 (0.02) | EGPEA 2 (p-Xylene 8) | 20 equiv (NaBAF 10 equiv) | 500 | 60 | 0.04 | Nd[b] | Nd | Nd |
| 49 | 15 (0.02) | None (p-Xylene 10) | 10 equiv (None) | 500 | 60 | 0.33 | — | $M_p$ = 956; $M_w$ = 52,382; $M_n$ = 817; PDI = 64.09 | 76.4 |
| 50 | 15 (0.02) | EGPEA 1 (p-Xylene 9) | 20 equiv (NaBAF 10 equiv) | 1000 | 120 | 0.06 | 4.8[a] 3.7IC 1.1EG | $M_n$ ($^1$H) = 6,329 | 52.6 |

[a]This number is an approximation due to the high homopolymer content of the sample;
[b]Nd: Not determined: Copolymer resonances, if present, are not distinguishable due to the presence of significant homopolymer resonances.

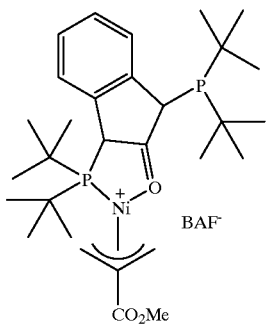

Example 51

Example 51 is listed in Table 3 below. The figure for compound 18 is shown above. The polymerization was carried out according to General Polymerization Procedure A. Varying amounts of acrylate homopolymer were present in some of the isolated polymers. In Table 3, the yield of the polymer was reported in grams and includes the yield of the dominant ethylene/acrylate copolymer as well as the yield of any acrylate homopolymer that was formed. Molecular weights were determined by GPC, unless indicated otherwise. Mole percent acrylate incorporation and total Me were determined by $^1$H NMR spectroscopy, unless indicated otherwise. Mole percent acrylate incorporation is typically predominantly IC, unless indicated otherwise.

Ligand and Catalyst Syntheses

The ligand for complex 18 was synthesized as follows: In a nitrogen-filled drybox, 2-indanone (0.50 g, 3.78 mmol) was placed in a round-bottom flask and dissolved in 20 mL of THF. Sodium hydride (0.77 g, 30.3 mmol) was added to the flask and the reaction mixture was stirred for approximately 1 h. Next, (t-Bu)$_2$PCl (1.37 g, 7.57 mmol) was added to the reaction mixture and stirring was continued overnight. The solution was filtered through a frit with Celite®. The solid was dissolved in pentane and filtered again to yield 1.59 g of a yellow powder. $^1$H NMR (CD$_2$Cl$_2$, diagnostic resonances) δ1.3–1.0 ppm (two major sets of doublets, P(t-Bu)).

The catalyst 18 was synthesized by stirring an Et$_2$O solution of the ligand (1 equiv), the appropriately substituted [(allyl)Ni(halide)]$_2$ precursor (0.5 equiv) and NaBAF (1 equiv) in a nitrogen-filled drybox for several hours. The solution was then filtered through a frit with dry Celite® and the solvent was removed in vacuo. The product was washed with pentane and then dried in vacuo. $^{31}$p NMR (C$_6$D$_6$): δ194,192, 190 (major), 185, 177, 70, 69, 48 (major), 31.

TABLE 3

Ethylene/Acrylate Copolymerization (0.02 mmol Ni Cmpd, 1 mL EGPEA, 9 mL Solvent, 20 equiv $B(C_6F_5)_3$, 10 equiv NaBAF, 1000 psi E, 18 h)

| EX | Catalyst | Solvent | Temp °C | Yield g | Acrylate Incorp. Mol % | M.W. | Total Me |
|---|---|---|---|---|---|---|---|
| 51 | 18 | p-Xylene | 120 | 1.04 | 1.0 0.43 IC 0.54 EG | $M_p$ = 988; $M_w$ = 1,719; $M_n$ = 780; PDI = 2.20 | 22.7 |

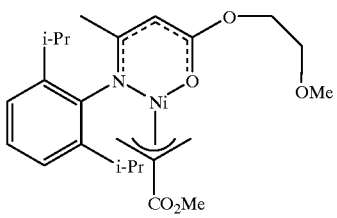

19

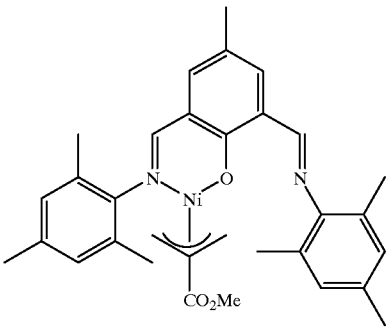

20

Example 52–53

Examples 52–53 are listed in Table 4 below. Figures for compounds 19 through 20 are shown above and procedures for making these Ni compounds and their ligand precursors are analogous to those reported in previously incorporated U.S. Pat. No. 6,174,975. In particular, the ligand for 18 was synthesized from 2-methoxyethyl acetoacetate and 1.2 equiv of 2,6-diisopropylaniline. The ligand for 20 was synthesized from 2-hydroxy-5-methyl-1,3-benzenedicarboxaldehyde and 2.2 equiv of 2,4,6-trimethylaniline. The ligands were deprotonated with NaH prior to reacting with $[(CH_2=C(CO_2Me)CH_2)Ni(\mu\text{-}Br)]_2$. The polymerizations were carried out according to General Polymerization Procedure A. Varying amounts of acrylate homopolymer are present in some of the isolated polymers. In Table 4, the yield of the polymer is reported in grams and includes the yield of the dominant ethylene/acrylate copolymer as well as the yield of any acrylate homopolymer that was formed. Molecular weights were determined by GPC, unless indicated otherwise. Mole percent acrylate incorporation and total Me were determined by $^1$H NMR spectroscopy, unless indicated otherwise. Mole percent acrylate incorporation is typically predominantly IC, unless indicated otherwise. The $LiB(C_6F_5)_4$ used (LiBArF) included 2.5 equiv of $Et_2O$.

TABLE 4

Ethylene/Acrylate Copolymerizations
(0.02 mmol Cmpd; 6.9 MPa E; 80° C.; 20 equiv $B(C_6F_5)_3$; 10 equiv LiBArF; 1 mL HA; 9 mL p-Xylene; 18 h)

| Ex. | Catalyst | Yield g | Acrylate Incorp. mol % | M.W. | Total Me |
|---|---|---|---|---|---|
| 52 | 19 | 0.015 | 0.2 | $M_n(^1H) = 1,124$ | 44.8 |
| 53 | 20 | 0.130 | 1.1 | $M_n(^1H) = 1,714$ | 99.3 |

Example 54

Values of LAIC for a Variety of Catalysts

The values of LAIC presented in Table 5 were obtained by constructing models of the complexes with Dreiding Models and measuring the respective angles and distances. The structures shown are to indicate the connectivity of the model, but the measurements were taken on the actual models.

TABLE 5

Examples of LAIC in selected complexes indicating mode of lithium binding.

$\theta = 130°, \lambda = 7$ Å        $\theta = 105°, \lambda = 5$ Å        $\theta = 95°, \lambda = 4.5$ Å

$\theta = 80°, \lambda = 3$ Å        $\theta = 75°, \lambda = 3$ Å        $\theta = 75°, \lambda = 3$ Å

TABLE 5-continued

Examples of LAIC in selected complexes indicating mode of lithium binding.

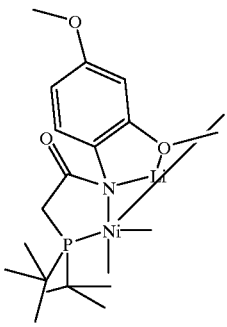

θ = 70°, λ = 3 Å

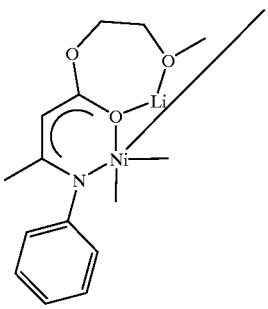

θ = 65°, λ = 3 Å

Examples 55–68

Examples 55–68 are listed in Tables 6–11 below. The figures for compounds 2–4 are shown below. The polymerizations were carried out according to General Polymerization Procedure A. Molecular weights were determined by GPC, unless indicated otherwise. Total Me were determined by $^1$H NMR spectroscopy, unless indicated otherwise.

TABLE 6

Conditions for Ethylene Polymerization and Copolymerization Screening.

| | |
|---|---|
| I | 0.02 mmol catalyst, 10 mL TCB, RT, 18 h, 6.9 MPa ethylene, 10 eq B(C$_6$F$_5$)$_3$ |
| II | 0.02 mmol catalyst, 10 mL TCB, RT, 18 h, 1.0 MPa ethylene, 10 eq B(C$_6$F$_5$)$_3$ |
| III | 0.02 mmol catalyst, 10 mL TCB, 60° C., 18 h, 1.0 MPa ethylene, 10 eq B(C$_6$F$_5$)$_3$ |
| IV | 0.02 mmol catalyst, 3 mL TCB, 2 mL E-10-U*, 60° C., 18 h, 1.0 MPa ethylene, 40 eq B(C$_6$F$_5$)$_3$ |
| V | 0.02 mmol catalyst, 9 mL TCB, 1 mL PMAO-IP (12.9 wt % (in Al) in toluene), RT, 18 h, 6.9 MPa ethylene |
| VI | 0.02 mmol catalyst, 4 mL TCB, 1 mL n-hexyl acrylate, 120° C., 18 h, 6.9 MPa ethylene, 40 eq B(C$_6$F$_5$)$_3$ |
| VII | 0.02 mmol catalyst, 10 mL TCB, 60° C., 18 h, 1.0 MPa ethylene, 10 eq B(C$_6$F$_5$)$_3$, 1 eq NaBAF |

*Ethyl-10-Undecylenate.

TABLE 7

| | | | Condition I in Table 6 | | | |
|---|---|---|---|---|---|---|
| Ex | Catalyst | Yield (g) | #Me/ 1000CH$_2$ | m.p. (° C.) (ΔH$_f$) | Mw/PDI | TON |
| 55 | 2 | 15.560 | 10 | 125 (218) | 13,921/4.91 | 27,734 |
| 56 | 3 | 11.718 | 14 | 124 (206) | 10,411/3.68 | 20,886 |
| 57 | 4 | 10.619 | 20 | 117 (185) | 2,792/2.57 | 18,927 |

TABLE 7-continued

| | | | Condition I in Table 6 | | | |
|---|---|---|---|---|---|---|
| Ex | Catalyst | Yield (g) | #Me/ 1000CH$_2$ | m.p. (° C.) (ΔH$_f$) | Mw/PDI | TON |

2

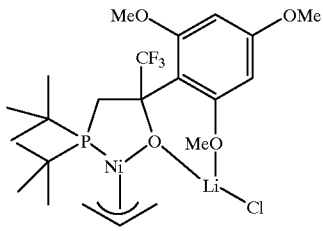

3

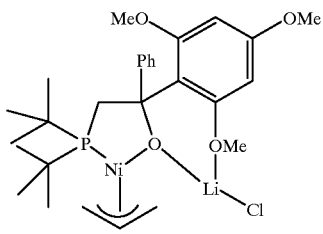

4

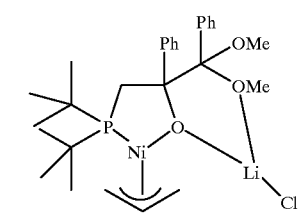

TABLE 8

Condition II in Table 6

| Ex | Catalyst | Yield (g) | #Me/ 1000 CH$_2$ | m.p. (° C.) (ΔH$_f$) | Mw/PDI | TON |
|---|---|---|---|---|---|---|
| 58 | 2 | 1.202 | 10 | 127 (181) | 52,542/4.3 | 2,142 |
| 59 | 3 | 2.631 | 30 | 120 (130) | 11,521/3.2 | 4,689 |
| 60 | 4 | 1.188 | 21 | 122 (207) | 6,405/3.2 | 2,117 |

TABLE 9

Condition III in Table 6

| Ex | Catalyst | Yield (g) | #Me/ 1000 CH$_2$ | m.p. (° C.) (ΔH$_f$) | Mw/PDI | TON |
|---|---|---|---|---|---|---|
| 61 | 2 | 6.624 | 13 | 124 (194) | 10,468/3.2 | 11,807 |
| 62 | 3 | 6.276 | 30 | 115 (198) | 5,285/3.6 | 11,186 |
| 63 | 4 | 4.196 | 32 | 115 (172) | 2,688/2.6 | 7,479 |

TABLE 10

Condition IV in Table 6

| Ex | Catalyst | Yield (g) | #Me/ 1000 CH$_2$ | Mole % Comonomer | m.p. (° C.) (ΔH$_f$) | Mw/PDI | TON E/EU* |
|---|---|---|---|---|---|---|---|
| 64 | 2 | 3.861 | 6 | 4.9 | 108 (92) | 6,315/2.5 | 4,939/257 |
| 65 | 3 | 0.129 | 12 | 5.1 | 124, 108 (124) | 7,435/4.0 | 164/9 |
| 66 | 4 | 0.268 | 16 | 4.8 | 88 (116) | 1,665/2.9 | 347/17 |

*Ethylene/Ethyl-10-undecylenate

TABLE 11

Condition VII in Table 6

| Ex. | Catalyst | Yield (g) | #Me/ 1000 CH$_2$ | m.p. (° C.) (ΔH$_f$) | Mw/PDI | TON |
|---|---|---|---|---|---|---|
| 67 | 2 | 13.547 | 18 | 122 (167) | 8,675/4.6 | 24,146 |
| 68 | 4 | 13.85 | 59 | 106 (110) | 3,033/3.3 | 24,700 |

We claim:

1. A process for polymerizing an olefin component comprising one or more polymerizable olefins, comprising the step of contacting, under polymerizing conditions, said olefin component with a polymerization catalyst system comprising a group 3–11 transition metal or lanthanide, a coordinating ligand, and a Lewis acid component, wherein the Lewis acid component is:
   (a) neutral and covalently bound to said coordinating ligand, or
   (b) positively charged and bound to a Lewis basic site of said coordinating ligand.

2. The process of claim 1, wherein the one or more polymerizable olefins are ethylene, H$_2$C=CH—(CH$_2$)$_t$—H, H$_2$C=CH—R$^{100}$—G, norbornene, substituted norbornene, cyclopentene and/or substituted cyclopentene, where t is an integer of 1 to 20, and R$^{100}$ is a covalent bond or alkylene or substituted alkylene, and G is an inert functional group.

3. The process of claim 2, wherein the one or more polymerizable olefins are ethylene and/or H$_2$C=CH—(CH$_2$)$_t$—H, wherein t is an integer of 1 to 20.

4. The process of claim 3, wherein ethylene alone is polymerized.

5. The process of claim 1, wherein the transition metal is a group 8–11 transition metal.

6. The process of claim 5, wherein the transition metal is Fe, CO, Pd, Ni or Cu.

7. The process of claim 1, wherein the Lewis acid component is positively charged and bound to a Lewis basic site of said coordinating ligand.

8. The process of claim 5, wherein said coordinating ligand is capable of holding said Lewis acid in close proximity to said metal component.

9. The process of claim 8, wherein the Lewis acid is bound to the complex within a Lewis Acid Interaction Cone of about 130° or less.

10. The process of claim 9, wherein the Lewis acid is bound to the complex within a Lewis Acid Interaction Cone of about 90° or less.

11. The process of claim 8, wherein a polar vinyl olefin is present.

12. The process of claim 11, wherein the polar vinyl olefin is copolymerized with a hydrocarbon olefin.

13. The process of claim 5, wherein the ligand is of the formula

(I)

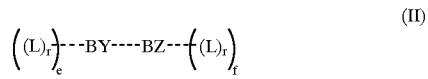

(II)

wherein BX, BY and BZ are each independently a Lewis base; L is independently LA or BX; LA is a Lewis acid; CA is a connecting atom selected from the group consisting of carbon, nitrogen, sulfur, silicon, boron, and phosphorus; f and r are independently an integer of 1 or more; e is zero or an integer of 1 or more; g is an integer of 2 or more; and dashed lines are bridges, single or multiple bonds.

14. The process of claim 13, wherein Formula (I) or (II) is

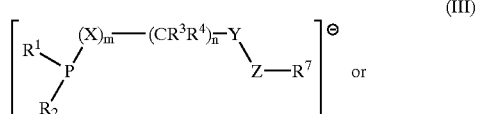

(III)

or

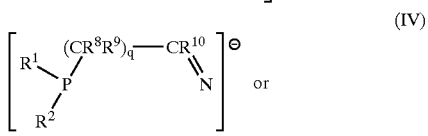

(IV)

-continued

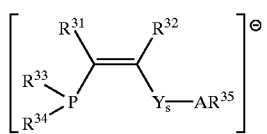
(V)

wherein:
R¹ and R² are each independently hydrocarbyl, substituted hydrocarbyl or a functional group;
Y is $CR^{11}R^{12}$, S(T), $S(T)_2$, P(T)Q, $NR^{36}$ or $NR^{36}NR^{36}$;
X is —O—, —$CR^5R^6$— or $NR^5$;
A is O, S, Se, N, P or As;
Z is O, S, Se, N, P or As;
each Q is independently hydrocarbyl or substituted hydrocarbyl;
$R^3$, $R^4$, $R^5$, $R^6$, $R^{11}$ and $R^{12}$ are each independently hydrogen, hydrocarbyl, substituted hydrocarbyl or a functional group;
$R^7$ is hydrogen, hydrocarbyl, substituted hydrocarbyl or a functional group, provided that when Z is O, S or Se, $R^7$ is not present;
each $R^8$ and $R^9$ is independently hydrogen, hydrocarbyl, substituted hydrocarbyl or a functional group;
$R^{10}$ is hydrogen, hydrocarbyl, substituted hydrocarbyl or a functional group;
$R^{11}$ and $R^{12}$ are each independently hydrogen, hydrocarbyl, substituted hydrocarbyl or a functional group;
each T is independently =O or =$NR^{30}$;
$R^{30}$ is hydrogen, hydrocarbyl, substituted hydrocarbyl, or a functional group;
each $R^{31}$ and $R^{32}$ is independently hydrogen, hydrocarbyl, substituted hydrocarbyl, or a functional group, provided that $R^{31}$ and $R^{32}$ taken together may form a ring;
$R^{33}$ and $R^{34}$ are each independently hydrocarbyl or substituted hydrocarbyl, provided that each is aryl substituted in at least one position vicinal to the free bond of the aryl group, or each has an $E_S$ of −1.0 or less;
$R^{35}$ is hydrogen, hydrocarbyl, substituted hydrocarbyl, or a functional group, provided that when A is O, S or Se, $R^{35}$ is not present;
$R^{36}$ is hydrogen, hydrocarbyl, substituted hydrocarbyl or a functional group;
m is 0 or 1;
s is 0 or 1;
n is 0 or 1; and
q is 0 or 1;
provided that:
any two of $R^3$, $R^4$, $R^5$, $R^6$, $R^8$, $R^9$, $R^{11}$ and $R^{12}$ bonded to the same carbon atom taken together may form a functional group;
any two of $R^1$, $R^2$, $R^3$, $R^4$, $R^5$, $R^6$, $R^7$, $R^8$, $R^9$, $R^{11}$, $R^{12}$, $R^{31}$, $R^{32}$, $R^{33}$, $R^{34}$, $R^{35}$, and $R^{36}$ bonded to the same atom or vicinal to one another taken together may form a ring.

15. The process of claim 14, wherein Formula (III)

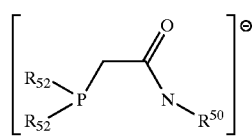
(VI)

or

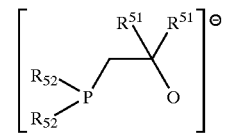
(VII)

wherein:
each $R^{52}$ is independently hydrocarbyl or substituted hydrocarbyl, provided that each $R^{52}$ is aryl substituted in one position vicinal to the free bond of the aryl group or each independently has an $E_S$ of −1.0 or less;
each $R^{50}$ is independently substituted hydrocarbyl; and
each $R^{51}$ is independently hydrogen, hydrocarbyl or substituted hydrocarbyl, provided that at least one of $R^{51}$ is substituted hydrocarbyl.

16. The process of claim 13, wherein Formula (I) or (II) is

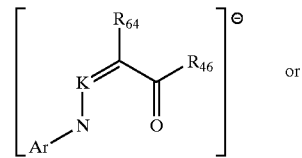
[VIII]

or

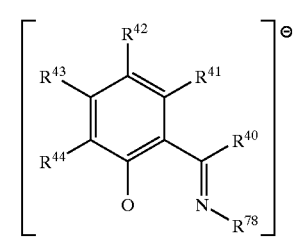
[IX]

wherein:
Ar is aryl or substituted aryl;
$R^{41}$, $R^{42}$, $R^{43}$ and $R^{44}$ are each independently hydrogen, hydrocarbyl, substituted hydrocarbyl or an inert functional group, and provided that any two of these groups vicinal to one another taken together may form a ring;
$R^{40}$ is hydrogen, hydrocarbyl or substituted hydrocarbyl;
K is N or $CR^{62}$;
$R^{46}$ is hydrocarbyl or substituted hydrocarbyl (such as —$SR^{67}$, —$OR^{67}$, or —$N(R^{68})_2$, wherein $R^{67}$ is hydrocarbyl or substituted hydrocarbyl, and each $R^{68}$ is independently hydrogen, hydrocarbyl or substituted hydrocarbyl);
$R^{64}$ is hydrogen, a functional group, hydrocarbyl or substituted hydrocarbyl, and $R^{62}$ is hydrocarbyl or substituted hydrocarbyl, provided that $R^{62}$ and $R^{64}$, or $R^{64}$ and $R^{46}$, taken together may form a ring; and
$R^{78}$ is hydrocarbyl or substituted hydrocarbyl.

17. The process of claim 13, wherein Formula (I) or (II) is

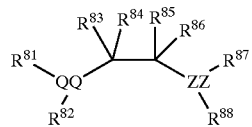

(X)

wherein:
ZZ is nitrogen or oxygen; and
QQ is nitrogen or phosphorous;
provided that:
when QQ is phosphorous and ZZ is nitrogen: $R^{81}$ and $R^{82}$ are each independently hydrocarbyl or substituted hydrocarbyl having an $E_S$ of about −0.90 or less; $R^{83}$, $R^{84}$, $R^{85}$, $R^{86}$ and $R^{87}$ are each independently hydrogen, hydrocarbyl or substituted hydrocarbyl; and $R^{88}$ is aryl or substituted aryl, provided than any two of $R^{81}$, $R^{82}$, $R^{83}$, $R^{84}$, $R^{85}$, $R^{86}$, $R^{87}$ and $R^{88}$ vicinal or geminal to one another together may form a ring;

when QQ is phosphorous and ZZ is oxygen: $R^{81}$ and $R^{82}$ are each independently hydrocarbyl or substituted hydrocarbyl having an $E_S$ of about −0.90 or less; $R^{83}$ and $R^{84}$ are each independently hydrogen, hydrocarbyl or substituted hydrocarbyl; $R^{85}$ and $R^{87}$ taken together form a double bond; $R^{88}$ is not present; and $R^{86}$ is hydrocarbyl or substituted hydrocarbyl (such as —$OR^{89}$ or —$NR^{90}R^{91}$, wherein $R^{89}$ is hydrocarbyl or substituted hydrocarbyl, and $R^{90}$ and $R^{91}$ are each independently hydrogen, hydrocarbyl or substituted hydrocarbyl);

when QQ is nitrogen: $R^{81}$ is hydrocarbyl or substituted hydrocarbyl having an $E_S$ of about −0.90 or less; $R^{82}$ and $R^{83}$ are each independently hydrogen, hydrocarbyl or substituted hydrocarbyl, or taken together form a ring or a double bond; $R^{84}$ is hydrogen, hydrocarbyl or substituted hydrocarbyl; ZZ is oxygen; $R^{86}$ and $R^{87}$ taken together form a double bond; $R^{88}$ is not present; $R^{85}$ is —$OR^{92}$, —$R^{93}$ or —$NR^{94}R^{95}$, wherein $R^{92}$ and $R^{93}$ are each independently hydrocarbyl or substituted hydrocarbyl, and $R^{94}$ and $R^{95}$ are each hydrogen, hydrocarbyl or substituted hydrocarbyl; provided that when $R^{82}$ and $R^{83}$ taken together form an aromatic ring, $R^{81}$ and $R^{84}$ are not present.

18. The process of claim 7, wherein the Lewis acid is lithium, sodium, potassium, magnesium, calcium, manganese, copper or zinc cation.

19. The process of claim 18, wherein the Lewis acid is lithium or sodium cation.

20. The process of claim 12, wherein ethylene is copolymerized with one or more of $H_2C$=$CH$—$(CH_2)_t$—H and/or $H_2C$=$CH$—$R^{100}$—G, the ethylene pressure is about 700 kPa or more, and said process is run at about 50° C. to about 170° C., where $R^{100}$ is a covalent bond or alkylene or substituted alkylene, and G is an inert functional group.

21. The process of claim 6, wherein the transition metal is nickel.

22. The process of claim 20, wherein the transition metal is nickel.

23. A process for polymerizing an olefin component comprising one or more polymerizable olefins, provided that at least one of said polymerizable olefins is a polar olefin, comprising the step of contacting, under polymerizing conditions, said olefin component with a polymerization catalyst system comprising a group 3–11 transition metal or lanthanide, a coordinating ligand, and a Lewis acid component, wherein the Lewis acid component is:
(a) neutral and covalently bound to said coordinating ligand, or
(b) positively charged and bound to a Lewis basic site of said coordinating ligand.

* * * * *